(12) United States Patent
Krasutsky et al.

(10) Patent No.: US 8,197,870 B2
(45) Date of Patent: Jun. 12, 2012

(54) DEPOLYMERIZATION EXTRACTION OF COMPOUNDS FROM BIRCH BARK

(75) Inventors: Pavel A. Krasutsky, Duluth, MN (US); Igor V. Kolomitsyn, Duluth, MN (US); Dmytro A. Krasutskyy, Duluth, MN (US)

(73) Assignee: Regents of the University of Minnesota, St. Paul, MN (US)

( * ) Notice: Subject to any disclaimer, the term of this patent is extended or adjusted under 35 U.S.C. 154(b) by 545 days.

(21) Appl. No.: 12/253,641

(22) Filed: Oct. 17, 2008

(65) Prior Publication Data

US 2009/0182158 A1    Jul. 16, 2009

Related U.S. Application Data

(63) Continuation of application No. PCT/US2007/066896, filed on Apr. 18, 2007.

(60) Provisional application No. 60/745,086, filed on Apr. 18, 2006.

(51) Int. Cl.
*A61K 36/00* (2006.01)

(52) U.S. Cl. .......... 424/769; 424/775; 424/725

(58) Field of Classification Search .......... None
See application file for complete search history.

(56) References Cited

U.S. PATENT DOCUMENTS

| | | | | |
|---|---|---|---|---|
| 4,732,708 A | * | 3/1988 | Ekman et al. | 554/138 |
| 5,804,575 A | * | 9/1998 | Pezzuto et al. | 514/169 |
| 6,392,070 B1 | | 5/2002 | Krasutsky et al. | |
| 6,634,575 B2 | * | 10/2003 | Krasutsky et al. | 241/19 |
| 2002/0028960 A1 | | 3/2002 | Krasutsky et al. | |
| 2002/0155177 A1 | | 10/2002 | Krasutsky et al. | |
| 2003/0153776 A1 | | 8/2003 | Sauter et al. | |

FOREIGN PATENT DOCUMENTS

| | | | |
|---|---|---|---|
| RU | 2074867 | | 3/1997 |
| RU | 2080326 C1 | | 5/1997 |
| RU | 2270202 C1 | | 2/2006 |
| RU | 2306318 | * | 9/2007 |
| SU | 0382657 | | 5/1973 |
| WO | WO-2007121482 A1 | | 10/2007 |

OTHER PUBLICATIONS

Kuznetsov et al. International Symposium on Wood and Pulping Chemistry. Jun. 1995. vol. 1, pp. 669-675, CAPLUS Abstract enclosed.*
Application Data for Russian Application No. 2006-237511, abstract, obtained from Database WPI Week 200625, Thomson Scientific, London, GB, (Feb. 20, 2006), 1 pg.
Application Data for Soviet Application No. 1974-18980V, abstract, obtained from Database WPI Week 197410, Thomson Scientific, London, GB, (Oct. 9, 1973), 1 pg.
European Application No. 07760861.0, Extended Search Report mailed Nov. 25, 2009, 6 pgs.

* cited by examiner

*Primary Examiner* — Christopher R. Tate
(74) *Attorney, Agent, or Firm* — Schwegman, Lundberg & Woessner P.A.

(57) ABSTRACT

The invention provides improved processes for the extraction of betulin, lupeol, betulinic acid, suberinic acids, and/or other organic compounds and compositions from birch bark. In some embodiments, the birch bark can be physically processed prior to the extraction process, which can further improve the yield of the extraction. The bark processing can include, but is not limited to, one or more of pelletizing the bark, baling the bark, pucking the bark, or compressing the bark, to a form that is more dense per volume unit than prior to the processing.

13 Claims, 5 Drawing Sheets

DEPOLYMERIZATION EXTRACTION OF COMPOUNDS FROM BIRCH BARK

RELATED APPLICATIONS

This application is a continuation under 35 U.S.C. 111 (a) of International Application No PCT/US2007/066896, filed Apr. 18, 2007 and published as WO 2007/121482 on Oct. 25, 2007, which claims priority under 35 U.S.C. §119(e) to U.S. Provisional Application No. 60/745,086, filed Apr. 18, 2006, which applications are incorporated herein by reference in their entirety.

FIELD OF THE INVENTION

The invention relates to processes for extraction of organic compounds from birch bark and to the products obtained from these processes.

BACKGROUND

Birch bark is a low-value waste product in the forest industry today. Ekman, R., *Holzforschung*, (1983) 37, 205. Approximately 230,000 tons of birch bark are generated per year. For example, a single paper mill can generate 70 tons of birch bark per day. Thus, vast quantities of birch bark and its chemical components are available.

Birch bark is a potential source of a variety of organic chemicals. Several triterpenoids have been identified in birch bark extracts. For example, lupeol, betulin, betulinic aldehyde, betulinic acid, methyl betulinate, lupenone, betulonic aldehyde, betulonic acid, β-amyrin, erythrodiol, oleanolic aldehyde, oleanolic acid, methyl leanolate and acetyl oleanolic acid are all present in the outer bark of *Betula verrucosa*. Eckerman, C., (1985) *Paperi ja Puu*, No. 3, 100. In addition, several suberinic acids, ω-hydroxy fatty acids, have also been identified in the bark of *Betula verrucosa*. Ekman, R., (1983), *Holzforschung*, 37, 205.

The chemical constituents of birch bark are useful in pharmaceutical and industrial applications. For example, U.S. Pat. No. 5,750,578 discloses that betulin possesses antiviral properties and is useful to treat herpesvirus. Betulin also possesses antifeedant activity against boll weevils, and anti-inflammatory activity (Miles, D. H., (1994), *J. Agric. Food. Chem.*, 42, 1561-1562, and Recio, (1995), M., *Planta Med.*, 61, 9-12. In addition, betulin showed cough suppressant and expectorant effects. Jinuhua, W., *Zhongguo Yaoxue Zazhi*, (1994), 29(5), 268-71. Betulin is also a useful starting material for preparing allobetulin and derivatives thereof, which possess useful pharmacological properties.

Betulin can be converted to betulinic acid, which is useful as a therapeutic agent. For example, Pisha, E. et al., (1995), *J. M. Nature Medicine,* 1, 1046-1051, discloses that betulinic acid has antitumor activity against human melanoma, e.g., MEL-1, MEL-2 and MEL-4. In addition, Fujioka, T. et al., (1994), *J. Nat. Prod.,* 57, 243-247 discloses that betulinic acid has anti-HIV activity in H9 lymphocytic cells.

Betulin has been extracted from the bark of white-barked birches in amounts up to 30%, based on the dry weight of the bark. Elkman, R., (1983), *Holzforsch,* 37, 205; Ohara, S., et al., (1986), *Mokuza Gakkaishi,* 32, 266. Additionally, betulin has been isolated from outer birch bark waste of *Betula verrucosa* by liquid extraction employing boiling organic solvents and subsequent recrystallization. Eckerman, C., (1985), *Paperi ja Puu*, No. 3, 100. While current processes afford betulin, these processes suffer from drawbacks. For example, the use of an organic solvent alone in the extraction of betulin may not result in the extraction of betulin that is found in a bound state in the birch bark, thus yielding less betulin than is actually present in the raw bark material.

Russian Patent Nos. RU2175326 (publication date 27 Oct. 2001) and RU2192879 (publication date 20 Nov. 2002), discloses methods of recovering betulin, and derivatives thereof, from birch bark. The methods disclosed in Russian Patent No. RU2192879 include birch bark milling, separation of birch bark fibers, solvent extraction of birch bark, separation of a solution from extracted birch bark, and removal of solvent from the extract. The extraction is carried out with toluene at temperatures of 90° C.-110° C. for 1.5-3.0 hours, and the solution is filtered at a temperature of 40° C.-50° C. The solution of betulin in toluene is cooled for 6-10 hours to a temperature of 15° C.-5° C. for crystallization of betulin.

Published U.S. Patent Application US 2003/0153776 A1 ("the '776 patent application") describes a process for obtaining betulin from birch bark. The process comprises extracting birch bark with a, water-immiscible solvent, and washing this extract with a dilute aqueous base, to provide betulin. Only a 4 wt. % yield of betulin is obtained by the process of the '776 patent application, and no other triterpenoids (e.g., lupeol, betulinic acid, or a combination thereof) are stated to be recovered. The use of charcoal, which is also believed to decrease the yield of betulin, is employed. The methods described in the '776 patent application are not able to effectively extract other naturally occurring triterpenoid derivatives such as betulin-3-caffeate, betulinic acid, or lupeol, or other organic materials such as esters of fatty acids, fatty acids, polyphenols, or tannins from the birch bark. Thus, the yields and purities of betulin resulting from the processes described in the '776 patent application have a need to be improved upon.

Another drawback to several of the currently used extraction processes employed to isolate betulin and other components in birch bark is that particularly hazardous organic solvents such as methylene chloride and chloroform are employed, which are toxic, carcinogenic, costly to dispose of, and pose a threat to the environment.

Thus, there exists a need for processes for recovery of betulin and other valuable natural organic compounds from birch bark that give higher yields of purer materials, use safer solvents, and minimize environmental hazards.

At least some of the inventors herein have previously disclosed and claimed other processes for isolation of natural products from birch bark. For example, see U.S. Pat. Nos. 6,392,070, 6,634,575, 6,768,016, and 6,815,553, and published application US 20050158414, all by Krasutsky, et al., which are incorporated herein by reference.

Suberins are another major component of birch bark. Suberins are a class of waxy water-insoluble polyester materials that are disposed in the birch bark. Kola, P. E. et al., (1981), *Ann. Rev. Plant. Physiol.,* 32, 539-67. Suberins are polyesters of hydroxylated fatty acids and polymeric polyphenolic constituents. In situ suberin is a macromolecular network insoluble in all solvents. The suberins of birch bark are typically polyesters of ω-hydroxy fatty acids with dicarboxylic fatty acids. These polyesters may further be hydroxylated or epoxidized. Ekman, *Holzforschung*, (1983), 37, 205-211.

Suberins possess several industrial applications. See, e.g., Taylor and Francis, (1998), *Forests Products Biotechnology*, A. Bruce and J. W. Palfreyman (editors), 167, 179-181; Peter E. Laks and Peggy A. McKaig, (1988), *Flavonoid Biocides: Wood Preservatives Based on Condensed Tannins, Horzforschung,* 42, 299-306; *Etherington & Roberts Dictionary*, definition of birch(bark), http://sul-server-2.stanford.edu/ don/dt/dt0328.html, 1, Jun. 23, 1999; P. E. Kolattukudy, (1981), Structure, Biosynthesis, and Biodegradation of Cutin and Suberin, *Ann. Rev. Plant Physiol.*, 32, 539-67, and N. Cordeiro, M. N. Belgasem, A. J. D. Silvestre, C. Pascol Neto, A. Gandini, (1998), "Cork Suberin as a new source of chemicals," *Int. Journal of Biological Materials*, 22, 71080. Suberin is useful as a dispersant in many industrial applications (e.g., carbon black slurries, clay products, dyes, cement, oil drilling muds, and asphalt emulsifiers). Suberin is also useful in binders for animal pellets, conditioners for boiling water, anti-oxidants and additives to lead-storage battery plate expanders. McGraw-Hill Concise Encyclopedia of Science & Technology, $4^{th}$ Ed., 1998.

Several fatty carboxylic acid derivatives, known collectively as suberinic acids, may be derived from saponification of suberin and other natural polyesters found in birch bark. The compound 9,10-Epoxy-18-hydroxyoctadecanoic acid is one such suberinic acid. Specifically, 9,10-Epoxy-18-hydroxyoctadecanoic acid has been found to protect leaves of a highly susceptible barley cultivar against fungal pathogen *Erysiphe graminis* f.sp. *hordei*. Sweitzer, P., et al., (1996), "Induction of Resistance in Barley Against *Erysiphe graminis* by Free Cutin Monomers," Physiol. Mol. Plant Pathol, 49(2), 103-120. This fatty acid derivative is of an usual type in nature in that it bears a hydroxyl group on the co-carbon, that is, the carbon at the distal end of the chain from the carboxylate moiety. Functionalization of this position of a fatty acid is unusual in nature, and is also difficult to achieve synthetically. Therefore, such compounds represent valuable intermediates for preparation of organic compounds.

Another suberinic acid which may be recovered from birch bark is 9,10,18-trihydroxyoctadecanoic acid. This compound is a useful precursor for the synthesis of ambrettolide. Ambrettolide (cis-hexadec-7-enolide), which is also found naturally occurring in the vegetable oil of ambrette seeds, is used as a musk fragrance in perfumes. The synthesis of ambrettolide may accomplished from 9,10,18-trihydroxyoctadecanoic acid via a high-yielding multi-step synthesis. Seoane, E., (1982), *J. Chem. Soc. Perkin Trans.*, 1837-1839.

A need therefore exists for environmentally safer, more cost-efficient methods to obtain commercial quantities of betulin, lupeol, betulinic acid, 9,10-epoxy-18-hydroxyoctadecanoic acid, and 9,10,18-trihydroxyoctadecanoic acid from birch bark.

SUMMARY

The invention provides a depolymerization extraction process for recovering a neutral organic compound from birch bark comprising first contacting the birch bark with a depolymerization mixture of an alkaline aqueous solution and a water-soluble organic solvent; then, optionally removing undissolved portions of the bark from the mixture, removing substantially all of the water-soluble organic solvent, adding a water-insoluble solvent, removing water, removing insoluble materials, removing a major proportion of the water-insoluble solvent; and lastly, recovering the neutral organic compound. Preferably, the process provides for extraction of betulin or lupeol or both from birch bark. Any suitable water-soluble organic solvent and water-insoluble solvent as defined herein may be used in the processes disclosed herein, but isopropanol or ethanol is preferred as the water-soluble solvent, and xylenes is preferred as the water-insoluble solvent. Water can be removed from the extract through azeotropic distillation with xylenes. Betulin is preferably purified by crystallization from the xylenes and subsequent filtration and drying, to yield about 16 to 18% of betulin of about 93 to 96% purity.

The step of first contacting the birch bark with a mixture of an alkaline aqueous solution and a water-soluble organic solvent according to the present invention provides an increased yield in a process for extraction of neutral organic compounds, for example betulin and lupeol, from birch bark, relative to a process where there is no such step of contacting with alkaline aqueous solution prior to or concurrently with extraction. The increased recovery of triterpene alcohols such as betulin and lupeol is an outstanding feature of the present invention. This increased recovery or yield is believed to be due to release of triterpene alcohols and other organic constituents from a polymeric matrix by depolymerization in conjunction with solvent extraction, from which matrix these substances would otherwise not be recovered by extraction alone. The hitherto unrecognized presence of polymer-bound triterpene alcohols, which was surprisingly found by the inventors herein, has been exploited according to the present invention through use of a depolymerization step prior to extraction, or concurrently with extraction, or both, to give significantly higher yields of neutral organic compounds, for example betulin, than would otherwise be achieved by solvent extraction of a given mass of birch bark without a preceding or concurrent step of alkaline depolymerization.

The invention herein further provides a process for recovering acidic organic compounds from the birch bark, the acidic organic compounds preferably comprising suberinic acids, betulinic acid, or both. Acidic organic compounds are likewise released, as their salts, from the polymeric matrix by alkaline depolymerization, enabling their recovery in a process according to the present invention. The salts of the acidic organic compounds may be subsequently neutralized with acid to provide the acidic organic compounds in free acid form.

The invention herein further provides a process for extracting betulin or lupeol, or both, from birch bark, comprising first contacting the bark with a mixture of a lower alcohol such as isopropanol or ethanol and an alkaline aqueous solution such as aqueous sodium or potassium hydroxide; then, optionally separating out undissolved portions of the bark, removing substantially all of the lower alcohol, adding a hydrocarbon solvent such as xylenes, removing substantially all the water, removing insoluble material; and lastly collecting an increased yield of betulin or lupeol or both from the hydrocarbon solvent. The process according to the present invention provides a yield of betulin from birch bark of about 16 to 18% at about 93 to 96% purity.

The invention herein further provides a process for extracting an acidic organic compound from birch bark, comprising first contacting the bark with a mixture of a lower alcohol such as isopropanol or ethanol and an alkaline aqueous solution such as aqueous sodium or potassium hydroxide; then, optionally removing insoluble portions of the bark, removing substantially all of the lower alcohol, adding a hydrocarbon solvent such as xylenes, removing substantially all the water, removing insoluble material; and lastly recovering the acidic organic compound in salt form from the insoluble material. The salt form of the acidic organic compound may be subsequently neutralized with acid to provide the acidic organic compound in free acid form. The process according to the present invention provides about a 22% yield of an acidic natural organic compound, the acidic natural organic compound preferably comprising suberinic acids or betulinic acid or depolymerized matrix of suberin, or a mixture thereof.

The invention further provides a compound comprising a neutral organic compound, the neutral organic compound being extracted from birch bark by a process comprising first contacting the bark with a mixture of an alkaline aqueous solution and a water-soluble organic solvent; then, optionally removing insoluble portions of the bark, removing substantially all of the water-soluble organic solvent, adding a water-insoluble solvent, removing water, removing insoluble material, removing a major proportion of the water-insoluble solvent; and lastly, recovering the neutral organic compound. The neutral organic compound preferably comprises betulin or lupeol, or both.

The invention further provides a compound comprising an acidic organic compound, the acidic organic compound being extracted from birch bark by a process comprising first contacting the bark with a mixture of an alkaline aqueous solution and a water-soluble organic solvent; then, optionally removing insoluble portions of the bark, removing substantially all of the water-soluble organic solvent, adding a water-insoluble solvent, removing water, removing insoluble material, removing a major proportion of the water-insoluble solvent; and lastly, recovering the acidic organic compound. The acidic organic compounds preferably comprises suberinic acids or betulinic acid, or both.

DETAILED DESCRIPTION

Figure 1A:
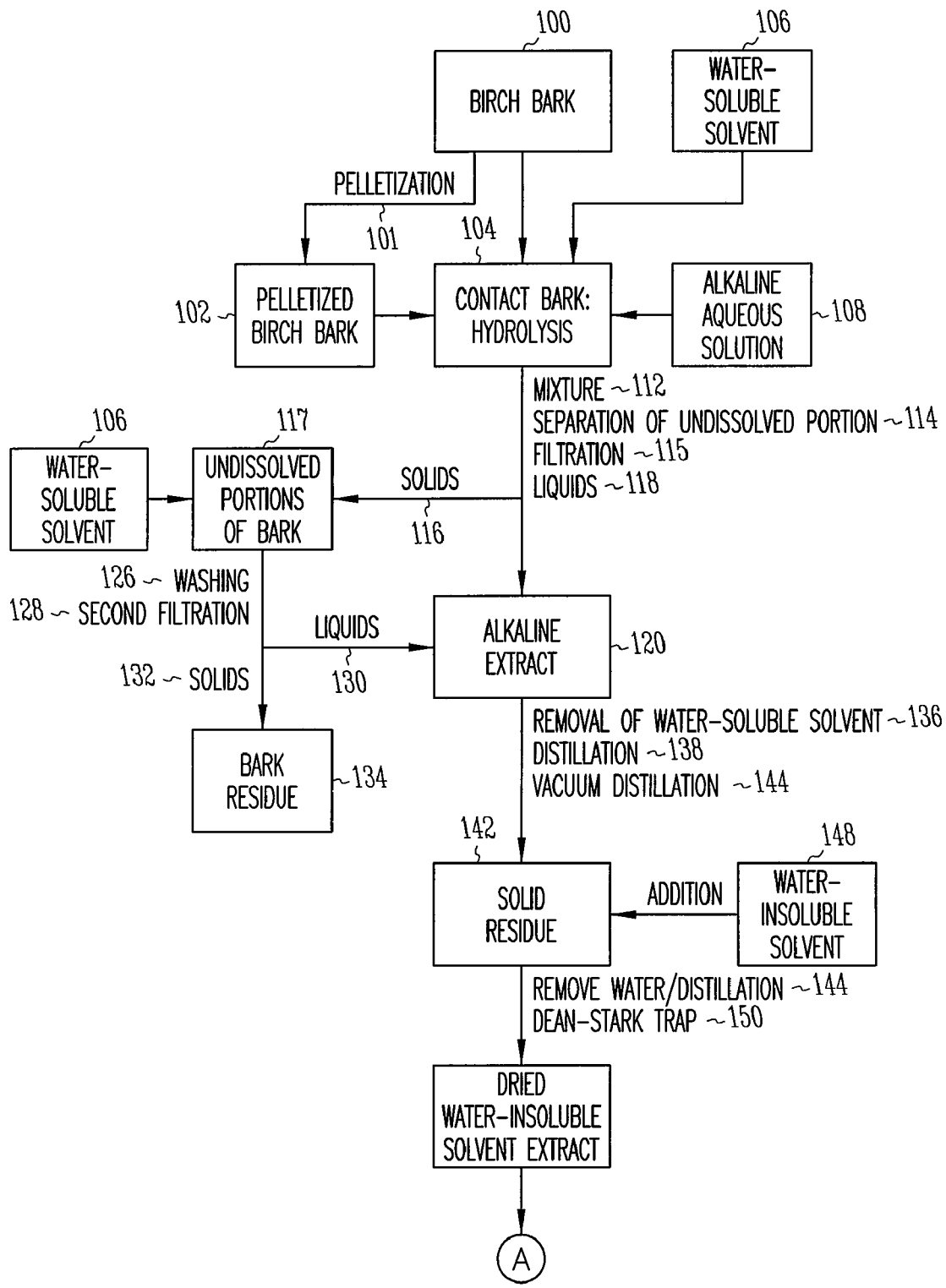
FIGS. 1A-1B are flow diagrams of a preferred embodiment of a depolymerization extraction process for recovering a neutral organic compound or an acidic organic compound, or both, from birch bark, according to the present invention.

As used herein, "birch" is any of the several deciduous trees of the genus *Betula*. The birches comprise the family Betulaceae in the order Fagales. Birch trees include, for example, white birch, *B. alba*; sweet, black or cherry birch, *B. lenta*; monarch birch, *B. maximowicziana*; dwarf or arctic birch, *B. nana*; Japanese white birch, *B. platyphyla Japonica*; smooth-bark birch, *B. pubescens*; yellow birch, *B. alleghaniensis*; paper, white or canoe birch, *B. papyrifera*; grey birch, *B. populifolia*; river birch, *B. nigra*; and the European birches, *B. pubescens; B. Alba* and *B. pendula*. Specifically, birch can be *B. alba, B. lenta, B. maximowicziana, B. nana, B. platyphyla Japonica, B. pubescens, B. alleghaniensis, B. papyrifera, B. populifolia, B. nigra, B. pubescens, B. Alba* or *B. pendula*. A specific birch for use in the processes of the present invention is *B. papyrifera*.

As used herein, "bark" refers to the dry outer covering of woody branches, stems and roots of plants that is very distinct and separable from the wood itself. It includes all tissue outside the cambium (growth layer between bark and wood). It is commonly understood to comprise tissue known as periderm.

As used herein, a "neutral organic compound" is any of the neutral natural products that are either present in birch bark or are produced from natural products present in birch bark by depolymerization extraction. Neutral organic compounds including neutral natural products are compounds that are not typically ionized or charged at around neutral pH (pH 7), and thus generally lack readily ionizable functional groups such as carboxylic acid groups or amino groups. The term neutral organic products specifically include triterpenoids such as betulin and lupeol that do not bear carboxylic acid groups, but do not include triterpenoid carboxylic acids, such as betulinic acid, or phenolic derivatives such as betulin caffeate, or suberinic acids, which are referred to herein as "acidic organic compounds."

As used herein, "triterpene" or "triterpenoid" refers to a plant secondary metabolite that includes a hydrocarbon, or its oxygenated analog, that is one of a class of compounds having approximately 30 carbon atoms and derived from six isoprene units via the biosynthetic intermediate squalene by a sequence of biologically-mediated cyclizations, functionalizations, and sometimes rearrangements. Most triterpenes are secondary metabolites in plants. Many are pentacyclic in structure, having five carbocyclic rings, each ring consisting of five or six carbon atoms. Examples of triterpenes include betulin, allobetulin, lupeol, friedelin, and all sterols, including lanosterol, stigmasterol, cholesterol, β-sitosterol, and ergosterol. Sterols generally are tetracyclic. Triterpenes or analogues thereof can be obtained by methods known in the art, i.e., using synthetic techniques or by isolation from plants. Examples of natural triterpenes and their biosynthetic routes are provided in, for example, R. B. Herbert, *The Biosynthesis of Secondary Plant Metabolites*, $2^{nd}$. Ed. (London: Chapman 1989).

As used herein, "betulin" refers to 3β,28-dihydroxylup-20 (29)-ene. Betulin is a pentacyclic triterpenoid found in the outer bark of paper birch trees (*Betula papyrifera, B. pendula*, etc.). It is known to be present at concentrations of up to about 24% of the bark of the white birch. Merck Index, twelfth edition, page 1236 (1996). Structurally, betulin is shown below:

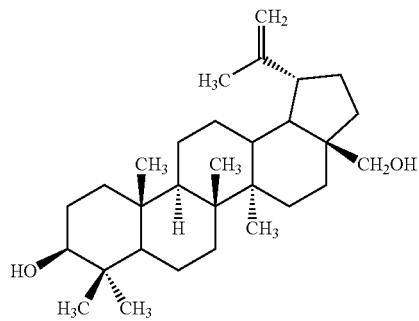

As used herein, "betulinic acid" refers to 3β-hydroxylup-20(29)-en-28-oic acid. Structurally, betulinic acid is shown below:

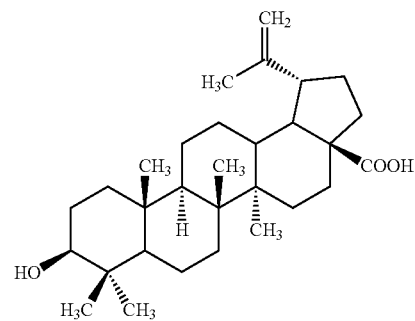

As used herein, "lupeol" refers to lup-20(29)-en-3β-ol. Lupeol is also found in birch bark and in other plant sources.

Lupeol is present at concentrations of about 1.5-3% of the birch bark and at up to about 8.2% in *Canavalia ensiformis*, a plant widespread in the humid tropics of Asia and Africa. Structurally, lupeol is shown below:

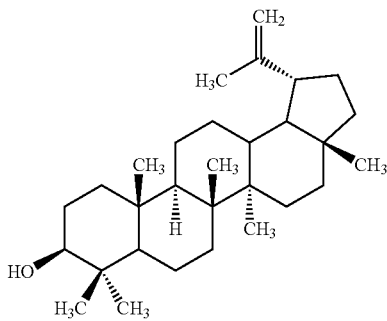

As used herein, an "acidic organic compound" refers to an acidic natural product, either in the form of a salt or of a free acid, that is naturally present in birch bark or is produced from a natural compound present in birch bark by hydrolysis (saponification), and comprises betulinic acid. An acidic organic compound also comprises suberinic acids, including 18-hydroxyoctadec-9-enoic acid, 9,10-epoxy-18-hydroxyoctadecanoic acid, 9,10,18-trihydroxyoctadecanoic acid (either the erythro or the threo form), 22-hydroxydocosanoic acid, docosandioic acid, and octadec-9-endioic acid.

The processes of the present invention provide neutral and acidic organic compounds from birch bark. Each organic compound may have one or more chiral centers and may exist in and be isolated in optically active and racemic forms. It is to be understood that the present invention provides processes for isolating organic compounds in any racemic, optically-active, polymorphic, or stereoisomeric form, present in the native bark or isolated after exposure to the processes of the invention. When a process of the invention provides a mixture of enantiomers or isomers, it is appreciated that those skilled in the art can separate optically active forms (for example, by resolution of the racemic form by recrystallization techniques or by chromatographic separation using a chiral stationary phase) if a single enantiomer is desired.

As used herein, "alkaline aqueous solution" refers to a solution in water of a substance that produces OH (hydroxide) ions in the aqueous solution. Specifically, the alkaline aqueous solution can include water, hydroxide ion, and at least one of a lithium ion ($Li^+$), a sodium ion ($Na^+$), a potassium ion ($K^+$), a calcium ion ($Ca^{2+}$), a magnesium ion ($Mg^{+2}$) and a barium ion ($Ba^+$). The solution is typically prepared by adding the solid metal hydroxide salt to the water solvent. More specifically, the alkaline aqueous solution includes at least one of sodium hydroxide (NaOH) or potassium hydroxide (KOH) dissolved in water.

As used herein, "water-soluble organic solvent" refers to organic solvents that are either miscible with water, i.e., soluble in all proportions, or alternatively are not miscible but do have sufficient water solubility to mix homogeneously with at least about 20% water by volume contained therein, such that the extraction medium comprising the mixture of the alkaline aqueous solution and the water-soluble organic solvent is homogeneous and does not phase-separate under the conditions used according to the processes of the present invention. An example of a water-soluble but not water-miscible solvent is sec-butanol. Water-soluble organic solvents further include lower alcohols such as methanol, ethanol, or isopropanol; lower ketones such as acetone, and cyclic ethers such as tetrahydrofuran or dioxane.

As used herein, "water-insoluble solvent" refers to a solvent that is substantially insoluble in water, i.e., that phase-separates from water at all concentrations of water above about 10% in the solvent. Diethyl ether is an example of a water-insoluble solvent according to the present definition that has a limited but finite capacity to dissolve water (about 6.9%). Other water-insoluble solvents include aliphatic hydrocarbons such as hexane, heptane, octane or nonane; aromatic hydrocarbons such as benzene, toluene or xylenes; halocarbons such as dichloromethane, chloroform, or trichloroethane; and oxycarbons such as higher acyclic ethers such as diisopropyl ether.

A preferred water-insoluble solvent is xylenes. As used herein, "xylenes" or "xylene" refers to all three positional isomers of dimethylbenzene, including ortho-, meta- and para-xylenes, referred to as o-, m- and p-xylenes respectively, or to any mixture of any two isomers or of all three isomers.

The processes of the present invention preferably comprise use of a water-insoluble solvent that (i) is capable of forming a low-boiling azeotropic mixture with water, or (ii) has a boiling point of at least 100° C. at atmospheric pressure, or both. In one embodiment, the solvent is capable of forming a low-boiling azeotropic mixture with water, such that azeotropic distillation is available as a means of removing water from the liquid phase being distilled. As used herein, "azeotropic distillation" refers to the distillation of a mixture of two materials, for example xylenes and water, wherein the boiling point of a defined vapor mixture (the azeotrope) is lower than the boiling point of either component alone.

In another embodiment, the water-insoluble solvent has a boiling point of at least 100° C. at atmospheric pressure, such that removal of water from a liquid mixture comprising the water-insoluble solvent and water may be accomplished by distillation of the solvent, which being hotter at its boiling point than the boiling point of water serves to remove water from the liquid medium by driving it off as a forerun. It is also within the scope of the invention that the water-insoluble solvent both has a boiling point at atmospheric pressure greater than 100° C. and also forms an azeotrope with water.

It is appreciated that those of skill in the art understand that the solvent should not chemically react with any of the starting materials or reagents present in the reaction mixture, to any significant degree, under the reaction conditions employed. For example, the solvent should not react to any appreciable degree with the alkaline aqueous solution present at the elevated temperatures typically employed during the steps of contacting the birch bark with the alkaline aqueous solution or of removing the water-soluble and the water-insoluble solvents. Therefore water-insoluble solvents such as esters, for instance, ethyl acetate or propyl butyrate, are not preferred water-insoluble solvents according to the present invention due to their tendency to hydrolyze under alkaline, high temperature conditions. Likewise, water-soluble organic solvents such as amides or nitriles, for example N,N-dimethylformamide or acetonitrile, are not preferred as water-soluble organic solvents due to their tendency to hydrolyze under alkaline, high temperature conditions.

As used herein, "separating" and "separation" refers to the process of removing solids from a liquid medium. The process can employ any technique known to those of skill in the art, e.g., filtration, centrifugation, decantation, or any other technique that can separate materials in the solid phase from materials in the liquid phase.

As used herein, "filtering" and "filtration" refers to the process of removing solids from a mixture by passing the liquid through a filter, usually a pad of fibrous or microporous solid material, thereby recovering the solids on the filter while allowing the liquid filtrate to pass through the filter. Filtration may be assisted either by increasing pressure upstream of the filter, as with gas pressure, or decreasing pressure downstream of the filter, as in vacuum filtration, or both.

As used herein, "distill," "distilling," and "distillation" refers to the process of extracting the volatile components from an at least partially liquid mixture by the condensation and collection of the vapors that are produced as the mixture is heated. The process typically includes the evaporation and subsequent collection by condensation of a liquid, but evaporation of a volatile component without subsequent condensation of the vapors may be used without departing from the principles of the invention. The evaporation may take place at atmospheric pressure or under reduced pressure. Typically distillation is carried out at the boiling point of the volatile component being extracted from the mixture, the boiling point being less when distillation under reduced pressure is employed. However evaporation may also take place at temperatures below the boiling point of the volatile component.

As used herein, "physical processing" of birch bark refers to processing that alters the natural physical form of the bark material. Birch bark is normally recovered in raw form during lumber-making operations as sheets or strips that are removed from the birch logs prior to sawing. "Physical processing" as used herein means chopping, grinding, comminuting, pelletizing, shredding, or otherwise altering the physical form to yield a product with a smaller average particle size, an increased surface area, increased uniformity, increased ease of handling, and increased extractability by solvents. "Physical processing" further includes forming bales ("baling"), sheets, rolls, or pucks or discs ("pucking") from the birch bark. The processing can increase the density of the form of the bark, which often makes the bark easier to transport, weigh, etc. The physical processing of bark can include formation of pellets from the bark, known as "pelletization" or "pelletizing" wherein relatively uniformly sized and shaped particles of bark are produced through mechanical operations carried out on the raw birch bark.

As used herein, the term "about" is intended to encompass variations in amounts of ingredients owing to variations in weighing and other measurement techniques, purity of ingredients, and the like, as would be known to the art worker. Such variations are often no more than about ±0.5%. The term "about" can indicate a variation of ±5 percent, or ±10 percent of the value specified; for example about 50 percent carries a variation from 45 to 55 percent; or the term can indicate ±1, 2, or 3 integers from the value specified.

As used herein, the term "substantially" or "substantially all of" refers to a majority of the term that is modified by "substantially". For example, the term "substantially" typically refers to greater than about 60%, greater than about 75%, greater than about 80%, greater than about 90%, greater than about 95%, greater than about 98%, greater than about 99%, greater than about 99.5%, greater than about 99.9%, or greater than about 99.99%.

In the claims provided herein, the steps specified to be taken in the claimed process may be carried out in any order without departing from the principles of the invention, except when a temporal or operational sequence is explicitly defined by claim language. Recitation in a claim to the effect that first a step is performed then several other steps are performed shall be taken to mean that the first step is performed before any of the other steps, but the other steps may be performed in any sequence unless a sequence is further specified within the other steps. For example, claim elements that recite "first A, then B, C, and D, and lastly E" shall be construed to mean step A must be first, step E must be last, but steps B, C, and D may be carried out in any sequence between steps A and E and the process of that sequence will still fall within the four corners of the claim.

Furthermore, in the claims provided herein, specified steps may be carried out concurrently unless explicit claim language requires that they be carried out separately. For example, a claimed step of doing X and a claimed step of doing Y may be conducted simultaneously within a single operation, and the resulting process will be covered by the claim. Thus, for example, a step of removing a water-soluble organic solvent, a step of removing water, and a step of removing a water-insoluble solvent may be conducted simultaneously or within a single process step, and that process will still fall within the four corners of a claim that recites those three steps.

Certain Embodiments of the Invention

Figure 1B:
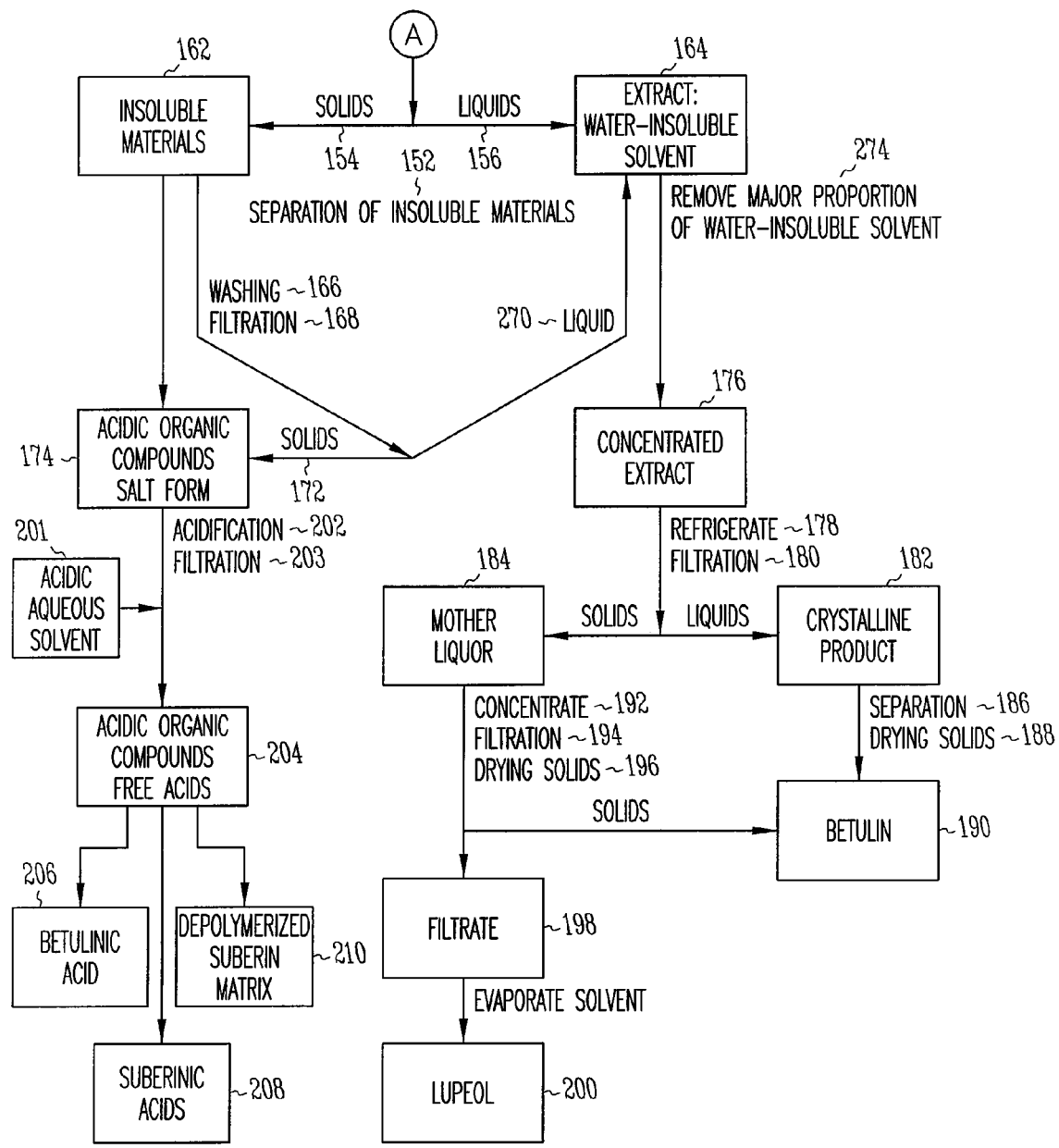

Referring to FIG. 1, a first preferred embodiment of a process for extracting a neutral organic compound from birch bark according to the present invention is shown. The birch tree bark 100, is preferably provided in pelletized form 102 by a step of pelletizing 101. As is well known in the art, birch bark is typically obtained from birch tree debarking operations, as during processing of birch logs into lumber, in the form of sheets or shreds of bark. Birch tree bark typically resembles a ream of thin sheets of paper in that the bark comprises multiple layers of individual sheets, which are somewhat adherent to each other. The sheets are typically of a somewhat waxy texture, due to the presence of natural products within the lignocellulosic sheets forming the birch bark. Typically, the bark of the birch tree may be removed from the underlying wood as a somewhat flexible sheet. Pelletization, that is, the formation of relatively uniformly sized and shaped particles of birch bark, is preferred as a technique of physical processing prior to contacting the birch bark with the extraction medium comprising the mixture of the alkaline aqueous solution and the non-aqueous water-soluble organic solvent. Pelletized birch bark is preferred to un-pelletized sheets or shreds of birch bark, based on factors such as uniformity of size and shape, ease of handling and transfer, minimization of dust formation, and improved contact with extraction solvents. Other preferred methods of physical processing prior to depolymerization extraction include formation of bales of birch bark (baling) or of discs or "pucks" of birch bark ("pucking"). However, birch bark that has not been pelletized or otherwise physically processed after removal from the birch tree, or birch bark that has been physically processed in ways other than baling, pucking, or pelletization, may be used without departing from the principles of the present invention.

In the step 104 of contacting the bark with a mixture of an alkaline aqueous solution 106 and a water-soluble organic solvent 108 to provide an extract, the bark is transferred to depolymerizer reaction vessel 110 after the vessel has been charged with the mixture 112 of the water-soluble solvent and the alkaline aqueous solution. The birch bark is then contacted with the mixture 112, the mixture preferably comprising a lower alcohol such as ethanol or isopropanol as the water-soluble solvent 106 and a water solution of sodium hydroxide or potassium hydroxide as the alkaline aqueous solution 108. Preferably the two liquids are mixed into the mixture 112 forming a single liquid phase prior to addition of the bark, preferably by stirring the mixture about a half hour at a temperature of about 50° C. Preferably the alkaline aqueous solution 108 comprises more than 30% by weight, and more preferably more than 60% by weight, of the solid sodium hydroxide or potassium hydroxide dissolved in water. However, the addition of the birch bark, the aqueous alkaline solution, and the water-soluble organic solvent may be carried out in any order without departing from the principles of the invention. The water-soluble organic solvent need not be soluble in water in all proportions, i.e. miscible, but the water-soluble organic solvent according to the present invention dissolves the alkaline aqueous solution without formation of a second phase, resulting in a homogeneous mixture 112.

The water-soluble organic solvent may comprise any solvent having sufficient water-solubility that is reasonably stable under the conditions preferably to be used, i.e., alkaline medium preferably at elevated temperatures. Thus, water-soluble organic solvents other than lower alcohols, for example lower ketones such as acetone or MEK, and cyclic ethers such as THF or dioxane, may be used without departing from the principles of the invention. Preferably the water-soluble organic solvent has a boiling point less than about 100° C., but greater than at least about 50° C.

During the step 104 of contacting the birch bark with the alkaline aqueous solution and the water-soluble organic solvent, depolymerization of natural esters disposed within the birch bark takes place. Esters formed from triterpenoid alcohols including betulin and lupeol in combination with the carboxylic acid groups of various other bark components such as suberinic acids, as well as esters of suberinic acid hydroxyl groups with suberinic acid carboxyl groups and esters of phenolic and carboxylic bark constituents with other molecular species, are depolymerized in the alkaline medium to yield compounds with free hydroxyl groups and free carboxylic acid groups (as their metal salts). The step of contacting thus brings about depolymerization, breaking down into lower molecular weight components the complex polymeric structures naturally existing in the bark. The depolymerization increases the quantity of bark components that may be recovered from the bark by extraction. The increased recovery of triterpene alcohols such as betulin and lupeol due to their release from the polymeric matrix, from which matrix they would otherwise not be recovered by solvent extraction, is an outstanding feature of the present invention. The hitherto unrecognized presence of polymer-bound triterpene alcohols, which was surprisingly found by the inventors herein, has been exploited according to the present invention by the depolymerization step prior to recovery of the neutral organic compounds to give significantly higher yields of betulin and lupeol than would otherwise be achieved by solvent extraction of a given mass of birch bark without hydrolysis.

The solid-liquid suspension formed by the mixture 112 and the birch bark 100 or pelletized birch bark 102 is contained within a depolymerizer reaction vessel 110 that is made of suitable materials to avoid corrosion of the vessel, particularly by the alkaline mixture. A preferred material of construction for the depolymerizer reaction vessel is stainless steel, although the vessel may be constructed of other materials such as glass-lined steel, corrosion-resistant metal alloys other than stainless steel such as Hastelloy®, glass, ceramic, or thermally-resistant plastics without departing from the principles of the invention. The depolymerizer reaction vessel is provided with mixing means such as an electrical or gas pressure powered motor driving a shaft equipped with one or more paddles, all made of suitably chemically resistant materials, to enable thorough mixing of the solid birch bark fragments or pellets with the alkaline mixture 112. The depolymerizer reaction vessel is also equipped with controllable heating means to allow for heating the mixture with or without the bark to a defined temperature and maintaining it at that temperature. The depolymerizer reaction vessel is further equipped with solvent vapor condensation means, for example a reflux condenser, to enable the mixture to be heated to the boiling temperature of the mixture 112 with the return of condensed solvent vapors to the reaction vessel, i.e., to reflux the mixture.

The mixture 112 held within the depolymerizer reaction vessel 110 is then heated to the boiling temperature of the mixture, typically around the boiling point of the water-soluble organic solvent. For a preferred water-soluble organic solvent, isopropanol, the boiling point is about 83° C. The mixture is stirred during the step of heating to boiling (reflux). The mixture is refluxed for a period of time, preferably about two to three hours, but shorter or longer times may be used without departing from the principles of the invention.

At the end of the period of time of contacting the bark 100 with the mixture 112, a step of separation 114 of undissolved portions of the bark from the suspension of the bark in the mixture is carried out. This step of separation 114 results in the separation of solid materials 116 comprising undissolved portions of the bark 117 from a liquid 118 comprising the water-soluble organic solvent, water, residual alkali, and organic materials extracted from the bark, comprising an alkaline extract 120.

These undissolved portions of bark 117 comprise materials such as cellulose, lignins, and other predominantly macromolecular substances that do not dissolve in the mixture 112 even after alkaline depolymerization. Preferably the step of separation 114 is carried out while the mixture is still at a temperature elevated above room temperature, but below the boiling temperature of the liquid, although the separation may be carried out at or even below room temperature without departing from the principles of the invention.

The step of separation 114 of the undissolved portions of the bark 117 from the alkaline extract 120 is preferably accomplished by means of a step of filtration 115. However, other means of separation such as centrifugation may be employed without departing from the principles of the invention. The step of filtration 115 is preferably accomplished by means of a filter 122 comprising a filter body containing a filter medium. The slurry of the undissolved solids 116 in the liquids 118 are transferred into the filter 122 by pumping, pouring, or any suitable means. The filter body and the filter medium are constructed of materials resistant to any corrosive effects of the extraction medium. The filter body is preferably constructed of stainless steel, although other corrosion-resistant metals such as Hastelloy®, glass, plastics, or ceramics are also suitable. The filter medium, which is selected to enable liquid materials to pass through while retaining the separated solid materials on the filter, may comprise paper; non-woven sheets formed of synthetic polymers; microporous polymer sheets; frits formed of metal, glass, plastics or ceramics; screens formed of metal or plastic; holed plates formed of metal, glass, plastics, or ceramics; or other forms and materials of construction that are suitable for carrying out the separation.

The step of filtration 115 may be assisted by the application of gas pressure to the headspace of the filter body, such that the gas pressure inside the filter body is increased, and the increased pressure differential between the headspace inside the filter body and the atmospheric pressure in the headspace of the filtrate receiving vessel 124, serves to increase the rate of filtration. Alternatively, a reduced pressure may be produced by any suitable means in the headspace of the filtrate receiving vessel 124 (vacuum filtration) and atmospheric pressure maintained in the filter body, or both techniques may be employed.

Preferably, as is shown in FIG. 1, the undissolved portions of the bark undergo a step 126 of washing with a water-soluble organic solvent, preferably the same water-soluble solvent 106. However, the step 126 of washing may be omitted without departing from the principles of the invention. The same water-soluble organic solvent as was used in the step of contacting the bark is preferred for the step of washing the undissolved portions of the bark. The step of washing may be carried out directly in the filter 122 by allowing the additional water-soluble organic solvent to pass through the undissolved portions of the bark 117, or the step may be carried out in a separate vessel wherein the undissolved portions 117 are suspended in the solvent, and the mixture then filtered in a second step of filtration 128.

The filtrate from the optional step of washing 126 is combined with the alkaline extract 120. The alkaline extract 120 comprises an extract of the depolymerized bark material in the water-soluble solvent 106. In order to recover the dissolved neutral organic compound and the dissolved acidic organic compound from the extract, the extract is further processed as described below.

In the first preferred embodiment according to the present invention as is depicted in FIG. 1, substantially all of the water-soluble organic solvent is then removed in a step 136 of removal of water-soluble solvent from the alkaline extract 120. Preferably the step 136 of removing substantially all of the water-soluble organic solvent is carried out using a step of distillation 138. The extract is transferred to a suitable distillation vessel 140 for the step of distillation. The distillation vessel is constructed of a suitable material as described above for the extraction vessel; stainless steel is preferred. The distillation vessel is equipped with stirring means, for example a paddle driven by an electric or gas pressure motor; a means for heating the vessel to the boiling point of the solvent being distilled; and a distillation head and condenser for removal of the solvent vapors from the headspace of the distillation vessel. The vessel 140 with contained alkaline extract 120 is heated until solvent boiling is initiated, and heating is continued until substantially all of the solvent 106 is removed. The distillation may be carried out under reduced pressure (vacuum distillation) without departing from the principles of the invention.

The solid residue 142 resulting from the removal of substantially all of the water-soluble organic solvent typically comprises a material with a sand-like consistency. This solid residue 142 comprises the neutral organic compound, and the acidic organic compound in salt form, in addition to residual water and alkali. Optionally, final removal of the water-soluble organic solvent may be accomplished by a step of vacuum distillation 144 under a partial vacuum in order to facilitate a more substantially complete removal of the solvent from the solid residue 142. The solid residue may optionally be further dried in a vacuum oven, preferably at about 25-20 mm Hg of vacuum and at a temperature of about 60-65° C., preferably for about 8 hours time. However, other degrees of vacuum, other temperatures, and other periods of time may be used without departing from the principles of the invention.

The solid residue 142 is transferred to an extraction vessel 146, and a water-insoluble organic solvent 148, preferably xylenes, is added to the vessel. Preferably about 6 L of water-insoluble solvent 148 is added per kilogram of solid residue 142, but other ratios may be used without departing from the principles of the invention. The extraction vessel 146 is constructed of suitable materials to withstand the organic solvent, elevated temperatures and alkaline conditions, preferably being constructed of stainless steel. The extraction vessel is equipped with stirring means, such as a paddle on a shaft driven by an electrical or gas pressure powered motor; controlled heating means, such as an electrically-powered heating mantle or an oil bath; distillation means, such as a distillation head and condenser, the distillation means preferably further comprising a water trap 150 of the Dean-Stark type. The preferred water-insoluble solvent xylenes forms an azeotrope with water upon distillation. The Dean-Stark water trap 150 provides a means for separation of water from the azeotrope condensate while allowing return of the water-insoluble solvent to the extraction vessel 146.

Once the solid residue 142 and the water-insoluble solvent 148 are charged to extraction vessel 146, they are allowed to remain in contact while water is removed, preferably by azeotropic distillation through a Dean-Stark trap as described above. The step 144 of distillation to remove water is accomplished when a preferred water-insoluble solvent that forms an azeotrope with water is employed. Alternatively, removal of water may be accomplished by distillation of a water-insoluble solvent that has a boiling point higher than that of water, that is, greater than 100° C. at atmospheric pressure. Removal of water by distillation may also be carried out under a partial vacuum without departing from the principles of the invention.

When xylenes is selected as the water-insoluble solvent 148, preferably a mixture of xylene isomers, i.e. a mixture of ortho-, meta-, and para-xylenes, is used. The use of a mixture of xylene isomers is preferred to use of a single isomer of xylene because, among other reasons, of the lower cost and the more favorable solvent properties of the mixed isomers over single isomers of xylenes. Whether single-isomer xylenes or mixed-isomer xylenes is used, however, removal of water is preferably accomplished by azeotropic distillation of water with the xylenes. The use of a Dean-Stark type water removal apparatus 150 is particularly preferred in removing water when xylenes is the solvent. Condensation of the vapors comprising the azeotropic mixture of water and xylenes results in phase separation of the two liquids. Water being the denser, the water phase will fall to the bottom of the receiver vessel, where in the Dean-Stark type apparatus it may readily be drawn off while the top xylenes layer is returned to the extraction vessel 146. In this manner distillation may be continued until substantially all the water is removed without needing to add additional makeup xylenes. Distillation is continued for a period of time after the bulk of the residual water has been removed, at least about a half an hour, so that virtually complete removal of water is accomplished.

According to the first preferred embodiment of a process for extracting neutral organic compounds from birch bark, as shown in FIG. 1, once the step 144 of removing water is complete, step 152 of separating insoluble material is carried out. The solid material 154 undissolved in the water-insoluble organic solvent is preferably removed by filtration, although other processes for separation of solid materials from liquids such as centrifugation may be used without departing from the principles of the invention. Preferably the step 152 of separation preferably by filtration is carried out after water removal is complete, but before the extract has cooled to ambient temperature.

The separation step 152 by filtration is accomplished by means of a filter 158 comprising a filter body containing a filter medium. The slurry of the liquid phase and the insoluble material are transferred into the filter 158. The filter body and the filter medium are constructed of materials resistant to the water-insoluble solvent medium. The filter body is preferably constructed of stainless steel, although other corrosion-resistant metals such as Hastelloy®, glass, plastics, or ceramics are also suitable. The filter medium, which as above is selected to enable liquid materials to pass through while retaining the separated solid materials on the filter, may comprise paper; non-woven sheets formed of synthetic polymers; microporous polymer sheets; frits formed of metal, glass, plastics or ceramics; screens formed of metal or plastic, holed plates formed of metal, glass, plastics, or ceramics; or other forms and materials of construction that are suitable for carrying out the separation. The filtration may be assisted by the application of gas pressure to the headspace of the filter body, such that the gas pressure inside the funnel is increased and the increased pressure differential between the headspace inside the filter body and atmospheric pressure, or even reduced pressure, in the headspace of the filtrate receiving vessel 160, serves to increase the rate of filtration.

Optionally, a step 166 of washing of the insoluble material with a portion of the same water-insoluble solvent is performed. Step 166 of washing may be carried out directly in the filter by adding the additional portion of the water-insoluble solvent 148 directly to the insoluble material, or alternatively the step 166 of washing may be carried out by suspending the insoluble materials in a vessel, adding the water-insoluble solvent, optionally stirring or agitating the suspension, and carrying out a second filtration 168. The filtrate of the washing is combined with the water-insoluble solvent extract filtrate 164 resulting from removal of the insoluble material 162.

In the first preferred embodiment according to the present invention, a neutral organic compound is recovered from the extract 164 resulting from the step 152 of separation by filtration. The neutral organic compound is recovered from the water-insoluble solvent extract 164 while an acidic organic compound is preferably recovered from the insoluble material 162 retained by the filter 158. Preferably the neutral organic compound comprises betulin or lupeol.

To recover the neutral organic compound, a step 174 of removal of a major proportion of the water-insoluble solvent 148 is carried out. The removal 174 of the water-insoluble solvent may be carried out by any technique that does not also remove or destroy the neutral organic compound. A major proportion of the water-insoluble solvent is preferably removed by distillation. The major proportion amounts to at least about 70% to about 100% of the total volume of the water-insoluble solvent.

Removal 174 of the major proportion of the water-insoluble solvent may comprise removal of all the water-insoluble solvent, resulting in a crude product comprising a neutral organic compound, which may be a solid or a liquid. The neutral organic compound may be purified from the crude product by any of the well-known means in the art, such as recrystallization, chromatography, trituration, and so forth. Preferably, however, removal of the major proportion of the water-insoluble solvent comprises removal of about 70% to about 90% of the total volume to provide a concentrated extract 176. More preferably this step of removal is followed by a step 178 of refrigeration and a step 180 of filtration. The step 174 of solvent removal and the step 178 of refrigeration are carried out such that upon cooling, the neutral organic compound undergoes crystallization, the crystalline product 182 being a solid. These steps are carried out such that the amount of the crystalline product 182 that is recovered is maximized, which may be done by adjusting the percentage of removal of water-insoluble solvent, the temperature to which the concentrated extract is cooled, and the time for which the refrigerated concentrated extract is held at the reduced temperature.

The recovery of the neutral organic compound comprises a step 186 of separation of the crystalline product 182 that has precipitated from the concentrated extract 176 after refrigeration. This step of separation 186 preferably comprises filtration, although other means of separation known in the art, such as centrifugation, may be used without departing from the principles of the invention. The filtration may be carried out as described above for the other steps of filtration. The crystalline product 182 typically comprises betulin 190 of about 93% purity, recovered in about an 18% yield based on the weight of starting birch bark 100.

The mother liquor 184 resulting from the step of separation of the crystalline product may optionally be further processed to recover additional betulin by additional concentration 192, filtration 194, and recovery of a second portion 196 of crystalline product, which comprises betulin 190. The second portion 196 typically comprises betulin in a less pure form than does the crystalline product 182. The second portion 196 may optionally be combined with the crystalline product 182 for further purification of betulin 190.

Preferably, filtrate 198 is further processed to recover a second neutral organic compound. Complete removal of the water-insoluble solvent from the filtrate 198 provides a second neutral organic compound comprising a lupeol fraction 201 typically comprising lupeol 200 of about 50% purity. Typically, the lupeol fraction 201 is recovered in about a 1.5% yield based on the weight of the starting birch bark. Lupeol may be further purified from fraction 201 by any of the techniques well-known to those skilled in the art, such as crystallization, chromatography, trituration, and so forth. A method of accomplishing this purification is disclosed in the published PCT patent application publication number WO2005/047304, which is incorporated herein by reference.

Neutral organic compounds betulin and lupeol are organic materials of the triterpenoid class that are valuable in commerce and may be used either in unchanged form or as precursors for the manufacture of valuable semi-synthetic organic compounds. Examples of uses include as additives to soaps, washing materials and cosmetics; skin-care and hair-care products; and to anti-fungal, anti-arthritis, anti-bacterial, anti-cellulitis, and anti-proliferative health care formulations.

In a preferred embodiment according to the present invention, an acidic organic compound is recovered from birch bark. Referring to FIG. 1, in a preferred embodiment of the process according to the present invention, an acidic organic compound in its salt form 174 is recovered from the insoluble material 162 resulting from the step 152 of separation by filtration as is described above.

The insoluble material is dried to provide an acidic natural organic compounds in its salt form 174. If sodium hydroxide was used in the preparation of the alkaline aqueous solution 108, it will be a sodium salt. If potassium hydroxide was used, it will be a potassium salt. An acidic organic compound in salt form 174 may be recovered from the insoluble material 162 by any of the techniques well-known to those persons skilled in the art, such as crystallization, chromatography, trituration, and so forth.

The acidic organic natural compound is preferably recovered via conversion to the free acid form 204 by a step 202 of acidification. The preferred method for recovery of an acidic natural organic compound in free acid form comprises treatment of the salt form with an acidic aqueous solution 201 followed by a step of filtration 203. Alternatively, the acidic organic compound in free acid form may be recovered by a step of solvent extraction without departing from the principles of the invention. The insoluble material 162 is suspended in an acidic aqueous solution 201, preferably a relatively dilute solution of a mineral acid in water. Preferably the mineral acid is hydrochloric acid, and the concentration of the hydrochloric acid in water is about 2% by volume. The salt form of the acidic organic compound is suspended in the 2% solution of hydrochloric acid in water contained within an acidifier vessel 205. A ratio of about 8 L of 2% hydrochloric acid per kilogram of insoluble material 162 is preferred. The acidifier vessel 205 is constructed of material that is resistant to the corrosive effects of the acid. Stainless steel or glass are preferred materials of construction. The solid material is stirred in the dilute hydrochloric acid solution for at least about 1 hour at ambient temperature, then is filtered to separate the acidic natural organic compounds as their free acids 204 from the aqueous solution containing inorganic salts and other water-soluble materials. The solid material may optionally be washed with water, then dried at a temperature preferably no greater than 45° C. until dry, typically not less than 15 hours. Alternatively, the free acid 204 may be recovered by solvent extraction, using any suitable solvent in which the free acid is soluble. An acidic organic compound comprises betulinic acid 206, or suberinic acids 208, or depolymerized matrix of suberin 210. Typically, a yield of about 22% of acidic natural organic compounds, comprising a mixture of betulinic and suberinic acids, is recovered. Typically, the suberinic acid fraction comprises 18-hydroxyoctadec-9-enoic acid, 9.10-epoxy-18-hydroxyoctadecanoic acid, 9,10,18-trihydroxyoctadecanoic acid (both erythro and threo forms), and 22-hydroxydocosanoic acid.

Figure 2A:
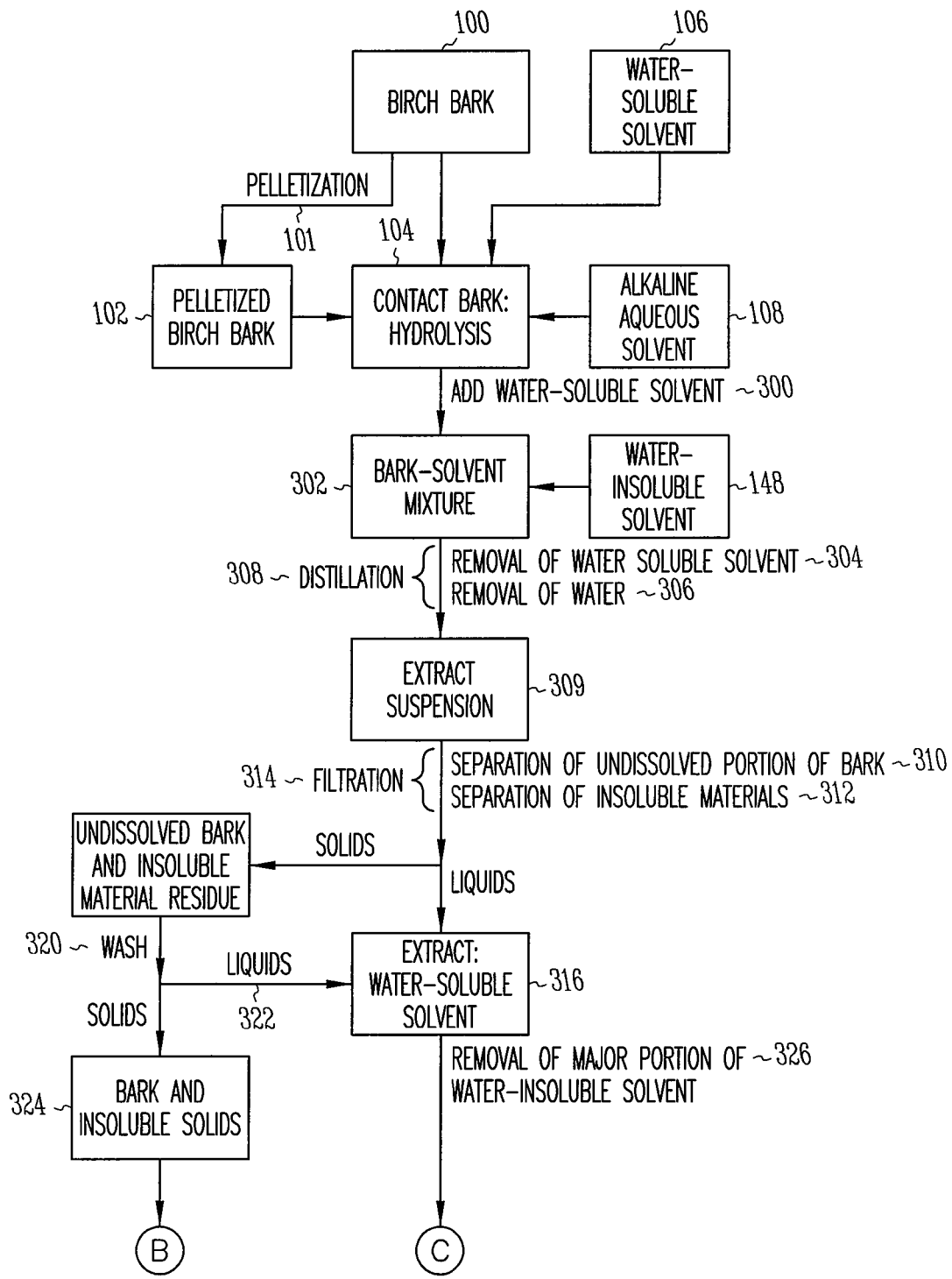
FIGS. 2A-2C are flow diagrams of a second preferred embodiment of a depolymerization extraction process for recovering a neutral organic compound or an acidic organic compound, or both, from birch bark, according to the present invention.
Figure 2B:
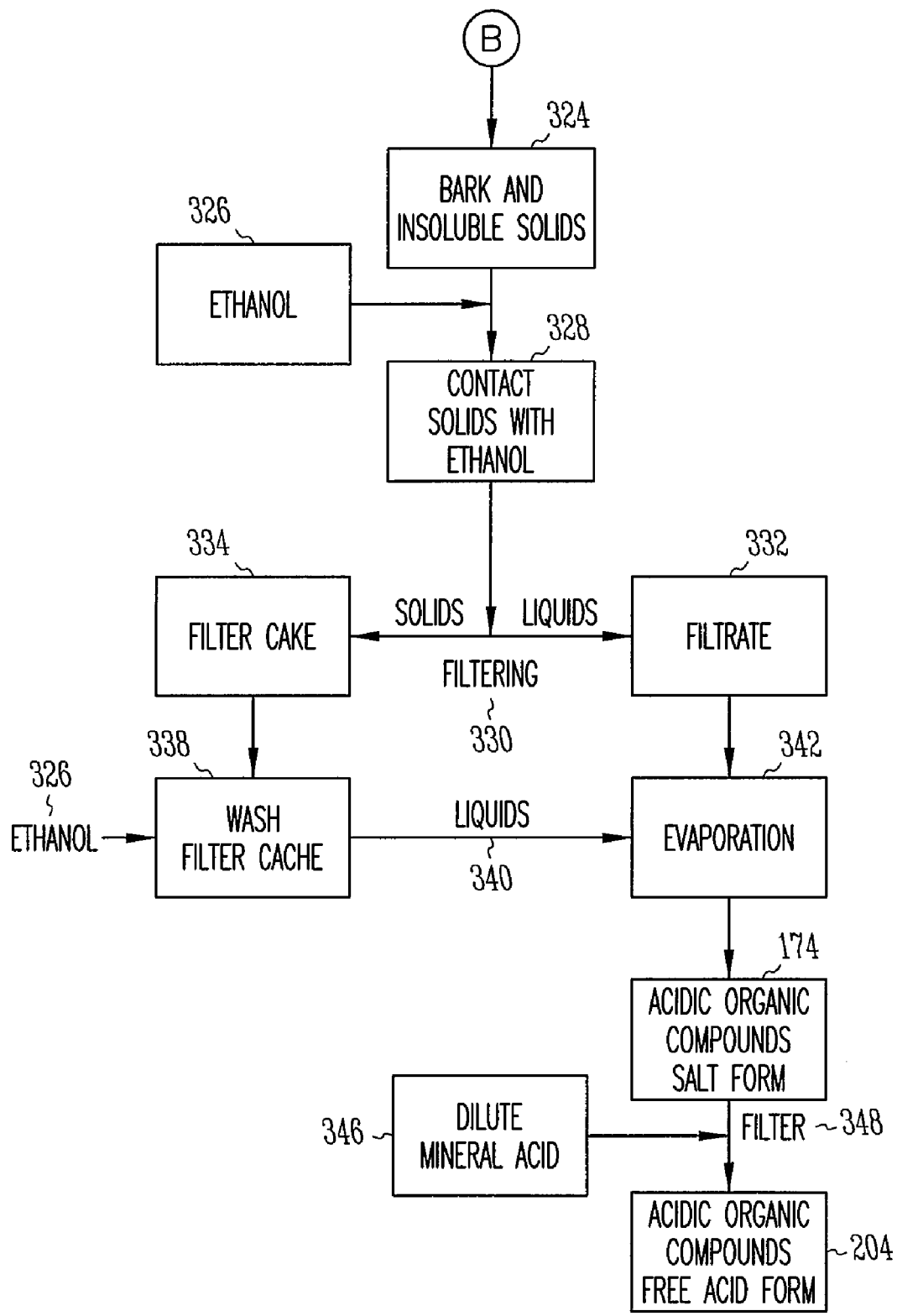
Figure 2C:
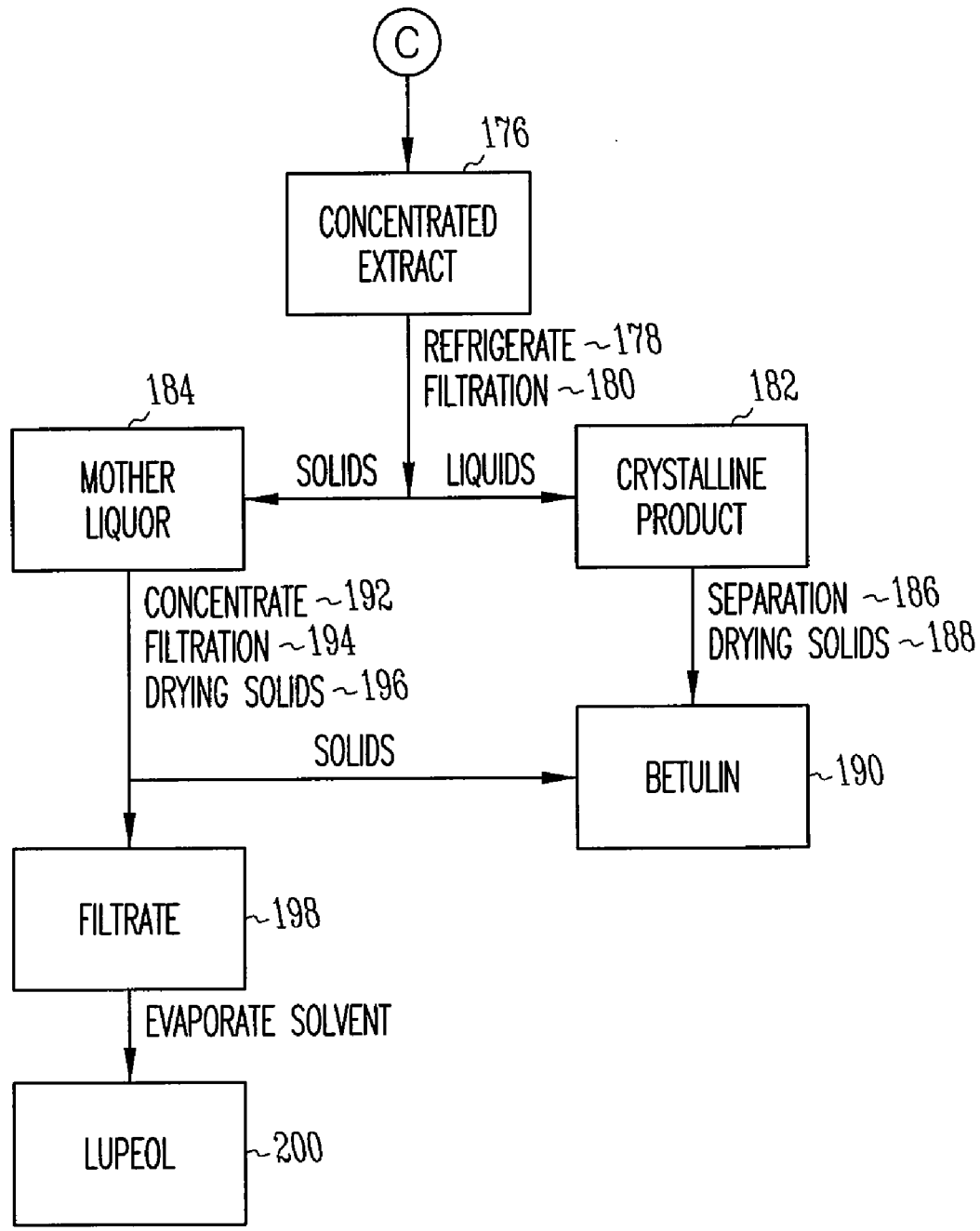

Referring to FIG. 2, a second preferred embodiment of a process for extracting a neutral organic compound or an acidic organic compound from birch bark according to the present invention comprises a one-pot process. The term "one-pot process" as used herein refers to a process wherein the number of separate vessels and transfers of materials between vessels that are required to practice the process are minimized to the greatest extent reasonably possible. In the second preferred embodiment, step 104 of contacting the birch bark 100 or preferred pelletized birch bark 102 with the depolymerization mixture of the alkaline aqueous solution 108 and the water-soluble organic solvent 106, preferably isopropanol or ethanol, is carried out in the same manner as in the first preferred embodiment, described above, including the optional pelletizing step 101. The preferred features of the alkaline aqueous solution and the water-soluble organic solvent, as well as preferred temperatures and times, for the step of contacting the mixture 112 are the same. The depolymerizer reaction vessel 110 is preferably constructed and configured as is described above for the first preferred embodiment, with the added feature that equipment for distillation such as a distillation head and a condenser are provided.

Then, a step 300 is taken of adding a water-insoluble solvent 148 to the mixture of the bark, the alkaline aqueous solution, and the water-soluble organic solvent, to provide a bark-solvent mixture 302. Preferably, the water-insoluble solvent comprises xylenes, preferably a mixture of xylenes isomers as is described above. According to the second preferred embodiment, undissolved portions of bark are not removed prior to addition of the water-insoluble solvent, therefore bark-solvent mixture 302 comprises undissolved portions of the bark, the water-solvent solvent 106, the alkaline aqueous solution 108, and the water-insoluble solvent 148. This mixture is contained within the depolymerizer reaction vessel 110.

Then, a step 304 of removing substantially all the water-soluble organic solvent and a step 306 of removing water are carried out together in the same step 308 of distillation, wherein the water, the water-soluble organic solvent, and a portion of the water-insoluble solvent are all distilled out of the depolymerizer reaction vessel 110. When the preferred water-soluble organic solvent isopropanol and the preferred-water insoluble solvent xylenes are used, isopropanol, having a boiling point of about 83° C., is the first material to distill out of the vessel 110. Then, as distillation continues at a higher temperature, the azeotrope of water and xylenes distills out. The boiling point of the azeotrope of water with, for example, m-xylene, is about 95° C.; the boiling point of the azeotrope of water with mixed xylenes is about 92° C. As distillation of the xylenes/water azeotrope continues, a Dean-Stark type water removal apparatus 150 may advantageously be employed as was described above. Distillation of the xylene/water azeotrope continues until removal of water is complete.

After accomplishing the steps of removing 304 the water-soluble organic solvent and of removing 306 water in the afore-described manner, an extract suspension 309 comprising undissolved portions of bark 117, insoluble materials comprising acidic organic compounds in salt form 174, and water-insoluble solvent 148 remains in the vessel 110. As used herein, "insoluble material" means components extracted from the bark that are not soluble in the water-insoluble solvent but had been previously in solution in the mixture of the alkaline aqueous solution and the water-soluble solvent but re-precipitated upon their removal, such as the acidic organic compounds in salt form, whereas "undissolved portions of bark" or "undissolved bark" refers to the lignocellulosic components of the bark that remain in solid form throughout the entire depolymerization extraction process.

Next, step 310 of separating undissolved portions of the bark and step 312 of separating insoluble material are carried out in the same operation. The mixture is subjected to a step 314 of filtration, providing a filtrate 316 comprising a bark extract dissolved in the water-insoluble solvent, and a filter cake 318 comprising undissolved bark and insoluble materials. A similar preferred type of filtration apparatus is used as was described above for the other steps of filtration. A step 320 of washing the separated solid material is carried out, comprising washing the undissolved portions of the bark and the insoluble material with xylenes, filtering, and combining the wash filtrate 322 with the water-insoluble solvent extract 316. The undissolved bark and insoluble materials solids 324 are preferably processed further to provide an acidic organic compound as is described below.

Recovery of a neutral organic compound from the extract 316, the neutral organic compound preferably comprising betulin 190 or lupeol 200, is carried out in the same manner as described above for the first preferred embodiment. A step 326 of removal of a major proportion of the water-insoluble solvent provides a concentrated extract 176. The concentrated extract 176 is further processed as was described above for the first preferred embodiment to provide neutral organic compounds, preferably betulin and lupeol. Typically, a yield of betulin of about 18%-19% of 97+% purity is achieved from the second preferred embodiment of the process according to the present invention. Lupeol may be recovered from the lupeol-containing fraction 201 by any of the techniques well-known to those skilled in the art, such as crystallization, chromatography, trituration, and so forth. A method of accomplishing this purification is disclosed in the published patent application publication number WO2005/047304, which is incorporated herein by reference.

Acidic organic compounds are recovered from the undissolved bark and insoluble materials solids 324 according to the second preferred embodiment by a step 328 of contacting the solids 324 with a lower alcohol, preferably ethanol 326. The step of contacting 328 preferably comprises a step of contacting at elevated temperatures, preferably by refluxing at the boiling point of the lower alcohol, preferably for a period of time of at least about one hour. A step of filtering 330 separates a liquid filtrate 332 and a solid filter cake 334. The solid filter cake is washed with additional ethanol, preferably with additional refluxing, and the liquids 340 are added to the filtrate 332 in the evaporation vessel 341. The solids may optionally be washing in the same manner an additional one or two times.

To recover the acidic organic compound in salt form, a step of evaporation 342 of the filtrate 332 plus the combined washes 340 is then carried out. The step of evaporation preferably comprises a step of distillation with recovery of the vapors of the volatile ethanol for reuse. Preferably the final stages of the step of evaporation is carried out under a partial vacuum, preferably with warming of the residue 344, to provide the acidic organic compound in salt form 174. Again, if the alkaline aqueous solution 108 comprised a solution of sodium hydroxide, the salt form 174 is the sodium salt; if 108 comprised a solution of potassium hydroxide, the salt form 174 is the potassium salt. The acidic organic compound may be used in the salt form, or alternatively it may be converted to the free acid form.

To provide the acidic organic compound in free acid form 204, the step of recovering the acidic organic compound further comprises a step of acidification 347. The residue 174 is treated with dilute aqueous acid 346, preferably dilute mineral acid such as 2% aqueous hydrochloric acid. The step of acidification may take place within the evaporation vessel 341, in which case the vessel is constructed of suitable materials that are resistant to the corrosive effects of the dilute mineral acid. Stainless steel is a preferred material of construction, but the vessel may be constructed of other materials such as glass without departing from the principles of the invention. The product from the step of acidification is separated from the liquid phase, preferably by a step of filtration 348. The step of filtration further comprises a step of washing of the solid acidic organic compound in free acid form 204 with water, and preferably further comprises a step of drying to provide a dry acidic organic compound in free acid form.

The acidic organic compound in free acid form 204 can comprise betulinic acid 206, suberinic acids 208, depolymerized suberin matrix 210, or a mixture thereof. When 204 comprises a mixture, it is understood that one of skill in the art would know of techniques where by the components of the mixture could be isolated and/or purified, including crystallization, chromatography, and the like.

Uses of the Neutral Organic Compound and of the Acidic Organic Compound

A neutral organic compound comprising triterpenoids extracted from birch bark can be formulated in various ways each suitable for a particular application or use of the compound. For example, it is known that betulin possesses antifungal medicinal compounds, so formulations comprising betulin suitable for treatment of fungal diseases are provided according to the present invention. A formulation comprising betulin for treatment of fungal diseases comprises a formulation suitable for skin care to be used in treating fungal diseases of the skin, or comprises a formulation suitable for hair care to be used in treating fungal infections of the scalp.

Acidic organic compounds betulinic and suberinic acids are organic materials, the first being of the triterpenoid class and the second of the linear fatty acid class, that are valuable in commerce and may be used either in unchanged form or as precursors for the manufacture of valuable semi-synthetic organic compounds. Examples of uses include as additives to soaps, washing materials and cosmetics; skin-care and hair-care products; and to anti-fungal, anti-arthritis, anti-bacterial, anti-cellulitis, anti-viral and anti-proliferative health care formulations. Thus, the compounds of the present invention have use in the treatment of skin malconditions caused be these pathogens. For instance, the compounds of the present invention may be used to treat Herpes virus, or the human immunodeficiency virus (HIV).

The neutral organic compounds and the acidic organic compounds can also be used as anti-proliferative agents. The term "anti-proliferative agent" as used herein is explained as follows. The normal cellular content of tissues and organs is maintained by a balance between cell division and cell death. Proliferative diseases are diseases resulting from a deregulation of the normal balance between these processes. Abnormally high numbers of cells in a tissue can arise either through increased levels of cell division (proliferation), or abnormally low levels of programmed cell death—or a combination of both. Abnormally high levels of cell proliferation can lead to the pre-malignant and malignant transformation of cells giving rise to cancer (for example, leukemias, sarcomas, adenomas, carcinomas, gliomas, melanomas, and so forth). Furthermore, the progression of cancer is facilitated by cellular events that inhibit normal pathways of programmed cell death. Abnormally high levels of cell proliferation and the consequent enhancement of extracellular matrix turnover can also significantly contribute to the pathogenesis of diseases other than cancer, including atherosclerosis, rheumatoid arthritis, psoriasis, idiopathic pulmonary fibrosis, scleroderma and cirrhosis of the liver. The neutral organic compounds and acidic organic compounds according to the present invention, and their derivatives and formulations, exert anti-proliferative effects both through the inhibition of cell division and the promotion of cell death, and that these functions will have beneficial effects on all of these diseases and cancers. Thus the compounds of the present invention have use as anti-cancer agents. Thus, the compounds isolated from birch bark by the processes according to the present invention comprise valuable medicaments for the treatment of these proliferative diseases.

EXAMPLES

Products were analyzed using gas chromatography/mass spectrometry (GC/MS). Sample preparation included methylation with a solution of $CH_2N_2$ in diethyl ether and silylation with bis(trimethylsilyl)trifluoroacetamide.

Example 1

Separate Stages of Depolymerization (NaOH) and Extraction

Preparation of Birch Bark Hydrolyzate

Pressed outer birch bark (15 kg) was added in portions to a solution of NaOH (3.5 kg, 87.5 mol) in $H_2O$ (1.75 L) and i-PrOH (150 L) at 50° C. The reaction mixture was refluxed for 3 hrs and then filtered. The solid portion recovered from the filter was refluxed with i-PrOH (60 L) for 0.5 hr and again filtered. The procedure was repeated a third time with 60 L of i-PrOH. The isopropanol extracts were combined and the solvent was evaporated yielding a solid residue I (7.9 kg). The solid residue I comprises the solid residue 142 of the preferred embodiment shown in FIG. 1.

Composition of I

| | |
|---|---|
| 18-Hydroxyoctadec-9-enoic acid, sodium salt | 6.4% |
| Threo-9,10,18-trihydroxyoctadecanoic acid, sodium salt | 6.7% |
| 18-Hydroxy-9,10-epoxyoctadecanoic acid, sodium salt | 20.5% |
| 22-Hydroxydocosanoic acid, sodium salt | 8.6% |
| Lupeol | 2.8% |
| Betulin | 43% |
| Betulinic acid, sodium salt | 3.0% |
| Other ω-hydroxy fatty acids, sodium salts | 9.0% |

Preparation of Crude Neutral Organic Compounds Extract

The solid residue I was added to an extractor containing xylenes (50 L). The mixture was refluxed for 1 hr. Water (1 L) was separated from the distillate using a Dean-Stark receiver. The xylenes solution was filtered at 100° C. and the solid part was transferred to an extractor with xylenes (10 L), and refluxed for an additional 1 hr. The second xylenes solution was filtered at 100° C. and the solid part was washed with additional xylenes (10 L). The combined xylenes extracts were concentrated by evaporation and the residue, consisting of a mixture of triterpenes, was dried under vacuum (200 mm Hg) at 80° C. for 8 hrs to yield the crude neutral extract II (3.33 kg). The crude neutral organic compounds extract II comprises the neutral organic compounds dissolved in xylenes of the concentrated extract 176 of the preferred embodiment shown in FIG. 1.

Composition of II: Lupeol 11.1%; Betulin 84%; Others 4.9%.

Preparation of Betulin 96%+

Product I was added to an extractor containing xylenes (50 L). The reaction mixture was refluxed for 1 hr. Water (1 L) was separated from the distillate using a Dean-Stark receiver. The xylenes solution was filtered at 100° C. and the solid residue was transferred to an extractor with xylenes (10 L), and refluxed for an additional 1 hr. The xylenes solution was again filtered at 100° C. and the solid residue was washed with xylenes (10 L). The combined xylenes extracts were concentrated by evaporation to a volume of about 35 L and the solute allowed to crystallize overnight at −15° C. The white precipitate was filtered off and the solid residue was washed twice with cold xylenes (1 L), then dried at 80° C. yielding III (2.4 kg). Product III comprises the betulin 190 of the preferred embodiment shown in FIG. 1.

Composition of III: Lupeol 1.7%; Betulin 96.4%; Others 1.9%.

Preparation of Lupeol Fraction

Product I was added to an extractor containing xylenes (50 L). The mixture was refluxed for 1 hr. Water (1 L) was separated from the distillate using a Dean-Stark receiver. The xylenes solution was filtered at 100° C. and the solid residue was transferred to an extractor with xylenes (10 L), and refluxed for 1 hr. The xylenes solution was filtered at 100° C. and solid residue washed with xylenes (10 L). The combined xylenes extracts were concentrated by evaporation to a volume of about 35 L and crystallized overnight at −15° C. The white precipitate was filtered and washed with cold xylenes (1 L) twice. The combined xylenes solutions were concentrated by evaporation to about 12 L and the solute allowed to crystallize overnight at −15° C. White precipitate was filtered off and washed twice with cold xylenes (0.2 L). Combined xylenes solutions were evaporated and dried in vacuum (200 mm Hg) at 80° C. for 8 hrs yielding IV (225 g). Product IV comprises lupeol 200 of the preferred embodiment shown in FIG. 1.

Composition of IV: Lupeol 34.5%; Betulin 9.8%; Others 55.6%.

Preparation of Suberinic and Betulinic Acids Sodium Salts

Product I was added to xylenes (50 L) and refluxed for 1 hr. Water (1 L) was separated from the distillate using a Dean-Stark receiver. The mixture was then filtered at 100° C. The solid residue recovered from the filter was transferred to an extractor and xylenes (10 L) were added. The mixture was refluxed for 1 hr, then the solution was filtered at 100° C. The solid residue from the filter was washed with xylenes (10 L) and dried at 80° C. to give V (4.49 kg). Product V comprises the acidic organic compounds salt form 174 of the preferred embodiment shown in FIG. 1.

Composition of V

| | |
|---|---|
| 18-Hydroxyoctadec-9-enoic acid, sodium salt | 12.5% |
| 18-hydroxy-9,10-epoxyoctadecanoic acid, sodium salt | 44.1% |
| Threo-9,10,18-trihydroxyoctadecanoic acid, sodium salt | 11.5% |
| 22-Hydroxydocosanoic acid, sodium salt | 10.3% |
| Betulinic acid, sodium salt | 12.2% |
| Other ω-hydroxy fatty acids, sodium salts | 9.4% |

Preparation of Suberinic and Betulinic Free Acids

Product V was acidified with a 2% solution of HCl in water (35 L) and the solution was then filtered. The solid residue recovered from the filter was washed twice with water (10 L) and dried at 40-45° C. in vacuum (200 mm Hg) for 8 hours to yield VI (3.38 kg). Product VI comprises the acidic organic compounds free acid form 204 of the preferred embodiment shown in FIG. 1.

Composition of VI

| | |
|---|---|
| 18-Hydroxyoctadec-9-enoic acid | 11.66% |
| 18-hydroxy-9,10-epoxyoctadecanoic acid | 44.6% |
| Threo-9,10,18-trihydroxyoctadecanoic acid | 11.3% |
| 22-Hydroxydocosanoic acid | 11.66% |
| Betulinic acid | 12.86% |
| Other ω-hydroxy fatty acids | 7.8% |

Example 2

Separate Stages of Depolymerization (KOH) and Extraction

Preparation of Birch Bark Hydrolyzate

Pressed outer birch bark (15 kg) was added in portions to a solution of KOH (4.2 kg, 75 mol) in $H_2O$ (2.25 L) and i-PrOH (80 L) at 50° C. The reaction mixture was refluxed for 3 hrs and then filtered. The solid residue was extracted twice with isopropanol (40 L). The isopropanol extracts were combined and the solvent evaporated, yielding a solid residue VII (10 kg). The solid residue VII comprises the solid residue 142 of the preferred embodiment shown in FIG. 1.

Composition of VII

| | |
|---|---|
| 18-Hydroxyoctadec-9-enoic acid, potassium salt | 5.8% |
| Threo-9,10,18-trihydroxyoctadecanoic acid, potassium salt | 11.5% |
| 18-hydroxy 9,10-epoxyoctadecanoic, potassium salt | 15.7% |
| 22-Hydroxydocosanoic acid, potassium salt | 7.4% |

| | |
|---|---|
| Lupeol | 3.4% |
| Betulin | 44% |
| Betulinic acid, potassium salt | 3.0% |
| Other ω-hydroxy fatty acids, potassium salts | 9.1% |

Preparation of Crude Neutral Organic Compounds Extract

The solid residue VII was added to an extractor containing xylenes (50 L). The mixture was refluxed for 1 hr. Water (1 L) was separated from the distillate using a Dean-Stark receiver. The reaction mixture was then filtered at 100° C. The solid residue recovered from the filter was added to an extractor with xylenes (10 L) and the mixture refluxed for 1 hr. The mixture was filtered at 100° C. and the solid residue was washed with xylenes (10 L). The combined xylenes extracts were concentrated by evaporation and the residue was dried under vacuum (200 mm Hg) at 80° C. for 8 hrs to yield the crude neutral extract VIII (3.01 kg). The crude neutral extract VIII comprises the neutral organic compounds dissolved in xylenes of the concentrated extract 176 of the preferred embodiment shown in FIG. 1.

Composition of VIII: Lupeol 7.1%; Betulin 87%; Others 5.9%.

Preparation of Betulin 96%+

The crude neutral extract VIII was added to an extractor containing xylenes (50 L). The mixture was refluxed for 1 hr. Water (1 L) was separated from the distillate using a Dean-Stark receiver. The mixture was filtered at 100° C. The solid residue recovered from the filter was added to an extractor containing xylenes (10 L) and the mixture was refluxed for 1 hr, then filtered at 100° C. The wash step was repeated. The combined xylenes extracts were concentrated by evaporation to about 35 L and the solute was allowed to crystallize overnight at −15° C. A white precipitate was recovered by filtration, washed twice with cold xylenes (1 L), and dried at 80° C. to yield IX (2.4 kg). The product IX comprises the betulin 190 of the preferred embodiment shown in FIG. 1.

Composition of IX: Lupeol 1.5%; Betulin 96.7%; Others 1.8%.

Preparation of Lupeol Fraction

Product IX was added to an extractor containing xylenes (50 L). The mixture was refluxed for 1 hr. Water (1 L) was separated from the distillate using a Dean-Stark receiver. The mixture was filtered at 100° C. The solid residue recovered from the filter was added to an extractor containing xylenes (10 L) and the mixture was refluxed for 1 hr, then was filtered at 100° C. The wash of the solid residue with xylenes (10 L) was repeated. The combined xylenes extracts was concentrated by evaporation to a volume of about 35 L, and the solute was allowed to crystallize overnight at −15° C. The white precipitate was separated by filtration, and the solid residue was washed twice with cold xylenes (1 L). The combined xylenes solutions were concentrated by evaporation to a volume of about 12 L and the solute allowed to crystallize overnight at −15° C. The precipitate was separated by filtration and the solid residue was washed twice with cold xylenes (0.2 L). The combined xylenes solutions were evaporated and the residue was dried under vacuum (200 mm Hg) at 80° C. at for 8 hrs to yield X (280 g). Product X comprises lupeol 200 of the preferred embodiment shown in FIG. 1.

Composition of X: Lupeol 40.9%; Betulin 9.1%; Others 49.9%.

Preparation of Suberinic and Betulinic Acids Potassium Salts

Product X was added to an extractor containing xylenes (50 L). The mixture was refluxed for 1 hr. Water (1 L) was separated from the distillate using a Dean-Stark receiver. The mixture was filtered at 100° C. The solid residue recovered from the filter was twice added to an extractor containing xylenes (10 L) and the mixture was refluxed for 1 hr, then filtered at 100° C. The solid residue recovered from the filter was dried at 80° C. to give XI (7.0 kg). Product XI comprises the acidic organic compounds salt form 174 of the preferred embodiment shown in FIG. 1.

Preparation of Suberinic and Betulinic Free Acids

Product XI was acidified with a 2% solution of HCl in water (35 L) and the solution was then filtered. The solid residue recovered from the filter was washed twice with water (10 L) then dried at 40-45° C. under vacuum (200 mm Hg.) for 8 hours to yield XII (5.28 kg). Product XI comprises the acidic organic compounds free acid form 204 of the preferred embodiment shown in FIG. 1.

Composition of XII

| | |
|---|---|
| 18-Hydroxyoctadec-9-enoic acid | 11.23% |
| 18-hydroxy-9,10-epoxyoctadecanoic acid | 34.3% |
| threo-9,0,18-trihydroxyoctadecanoic acid | 14.9% |
| 22-Hydroxydocosanoic Acid | 14.99% |
| Betulinic acid | 5.8% |
| Other ω-Hydroxy fatty acids | 18.2% |

Example 3

One-Pot Depolymerization (NaOH) and Extraction

Preparation of Crude Neutral Organic Compounds Extract

Pressed outer birch bark (1 kg) was added in portions to a solution of NaOH (230 g, 5.75 mol) in $H_2O$ (90 ml) and EtOH (2.5 L) at 70° C. The reaction mixture was refluxed with good stirring for 1 hr. Xylenes (6 L) was then added, and a mixture of EtOH and $H_2O$ in xylenes (3.6 L) was distilled from the reaction mixture. Distillation was continued until the temperature of the vapors reached 133° C. An additional amount of $H_2O$ (15 ml) was distilled from the reaction mixture using a Dean-Stark receiver. The reaction mixture was filtered at 100° C. The solid residue was added to xylenes (3 L) and refluxed for 1 hr. Water (15 ml) was distilled from the reaction mixture using a Dean-Stark receiver, and the reaction mixture was filtered at 100° C. Washing of the solid residue with xylenes (3 L) was repeated. The combined xylenes extracts was evaporated and the residue dried in vacuum at 80° C. to give XIII (200 g). The crude neutral organic compounds extract XIII comprises the neutral organic compounds dissolved in xylenes of the concentrated extract 176 of the preferred embodiment shown in FIG. 2.

Composition of XIII: Lupeol 5.7%; Betulin 88.8%; Others 5.5%.

Preparation of Betulin 97%+

Pressed outer birch bark (1 kg) was added in portion to a solution of NaOH (230 g, 5.75 mol) in $H_2O$ (90 ml) and EtOH (2.5 L) at 70° C. The reaction mixture was refluxed with good stirring for 1 hr. Xylenes (6 L) was then added to the reaction mixture. A solution of EtOH and $H_2O$ in xylenes (3.6 L) was distilled from the reaction mixture. Distillation was continued until the temperature of the vapors reached 133° C. An additional amount of $H_2O$ (15 ml) was distilled from the reaction mixture using a Dean-Stark receiver. The mixture was filtered at 80° C. The solid residue recovered from the filter was added to xylenes (3 L) and refluxed for 1 hr. Water (15 ml) was distilled from the reaction mixture using a Dean-Stark receiver, and the reaction mixture was filtered at 80° C. Washing of the solid residue with xylenes (3 L) was repeated.

The combined xylenes extracts were heated and a portion of the xylenes (6 L) was removed by distillation. Betulin was allowed to crystallize from the xylenes solution at room temperature overnight, then was recovered by filtration, and dried under vacuum at 80° C. to give XIV (170 g, 17%). The product XIV comprises the betulin 190 of the preferred embodiment shown in FIG. 2.

Composition of XIV: Lupeol 1%; Betulin 97%; Others 2%.

Preparation of Lupeol Fraction

Pressed outer birch bark (1 kg) was added in portions to a solution of NaOH (230 g, 5.75 mol) in $H_2O$ (90 ml) and EtOH (2.5 L) at 70° C. The reaction mixture was refluxed with good stirring for 1 hr. Xylenes (6 L) was then added to the reaction mixture. A solution of EtOH and $H_2O$ in xylenes (3.6 L) was distilled from the reaction mixture. Distillation was continued until the temperature of the vapors reached 133° C. An additional amount of $H_2O$ (15 ml) was distilled from the reaction mixture using a Dean-Stark receiver. The reaction mixture was filtered at 80° C. and the solid residue recovered from the filter was added to xylenes (3 L) then refluxed for 1 hr. Water (15 ml) was distilled from the reaction mixture using a Dean-Stark receiver, and the reaction mixture was filtered at 80° C. Washing of the solid residue with xylenes (3 L) was repeated. The combined xylenes extracts were heated and a portion of the xylenes (6 L) was evaporated. Betulin was allowed to crystallize from the xylenes solution at room temperature overnight. The xylenes solution was filtered and solid part was dried in vacuum at 80° C. to give betulin (170 g, 17%, purity is 97%). The mother liquor was concentrated by evaporation to a volume of about 150 ml, and additional betulin was allowed to crystallize from the mother liquor at room temperature. After filtration, the solid part was dried in vacuum at 80° C. to give betulin (10 g, 1%, purity is 67%). The mother liquor was evaporated and dried under vacuum at 80° C. to give XV (20 g, 2%). Product XV comprises lupeol 200 of the preferred embodiment shown in FIG. 2.

Composition of XV: Lupeol 64%; Betulin 4.6%; Others 31.4%.

Preparation of Suberinic and Betulinic Acids Sodium Salts

Pressed outer birch bark (1 kg) was added in portions to a solution of NaOH (230 g, 5.75 mol) in $H_2O$ (90 ml) and EtOH (2.5 L) at 70° C. The reaction mixture was refluxed with good stirring for 1 hr. Xylenes (6 L) was then added to the reaction mixture. A solution of EtOH and $H_2O$ in xylenes (3.6 L) was distilled from the reaction mixture. Distillation was continued until the temperature of the vapors reached 133° C. An additional amount of $H_2O$ (15 ml) was distilled from the reaction mixture using a Dean-Stark receiver. The reaction mixture was filtered at 80° C. The solid residue was added to xylenes (3 L) and refluxed for 1 hr. Water (15 ml) was distilled from the reaction mixture using a Dean-Stark receiver and the mixture was filtered at 80° C. Washing of the solid residue with xylenes (3 L) was repeated. The solid residue after extraction with xylenes was added to ethanol (8 L) and refluxed for 1 hr, then filtered at 70° C. The solid part was then twice added to ethanol (4 L) and refluxed for 1 hr, then again filtered at 70° C. The combined ethanol solutions were evaporated and dried under vacuum at 80° C. to give XVI (330 g). Product XVI comprises the acidic organic compounds salt form 174 of the preferred embodiment shown in FIG. 2.

Composition of XVI

| | |
|---|---|
| 18-Hydroxyoctadec-9-enoic acid, sodium salt | 11% |
| 18-Hydroxy-9,10-epoxyoctadecanoic acid, sodium salt | 44% |
| Threo-9,10,18-trihydroxyoctadecanoic acid, sodium salt | 12% |
| 22-Hydroxydocosanoic acid, sodium salt | 11% |
| Betulinic acid, sodium salt | 11% |
| Other hydroxy Fatty acids sodium salts | 10% |

Preparation of Suberinic and Betulinic Free Acids

Pressed outer birch bark (1 kg, d=0.6 g/ml) was added portionally to a solution of NaOH (230 g, 5.75 mol) in $H_2O$ (90 ml) and EtOH (2.5 L) at 70° C. The reaction mixture was refluxed with good stirring for 1 hr. Xylenes (6 L) was then added to the reaction mixture. A solution of EtOH and $H_2O$ in xylenes (3.6 L) was distilled from the reaction mixture. Distillation was continued until temperature of vapors reached 133° C. An additional amount of $H_2O$ (15 ml) was distilled from the reaction mixture by using a Dean-Stark receiver. The reaction mixture was filtrated at 80° C. Solid part was added to xylenes (3 L) and refluxed for 1 hr. $H_2O$ (15 ml) was distilled from the reaction mixture by using a Dean-Stark receiver and the reaction mixture was filtrated at 80° C. Washing of solid part with xylenes (3 L) was repeated. Solid part after extraction with xylenes were added to ethanol (8 liters) and refluxed for 1 hour. The reaction mixture was filtrated at 70° C. and solid part was added to ethanol (4 L) and refluxed for 1 hr. The reaction mixture was filtrated at 70° C. and solid part was extracted with ethanol (4 L) using the same procedure as is it was described above. Ethanol solutions were combined, evaporated from solvent and dried in vacuum at 80° C. to give the acids as their sodium salts (330 g), which, was acidified with a 2% solution of HCl (2.3 L) and filtered. The solid residue was washed twice with water (10 L) and dried in vacuum (200 mm Hg) at 40-45° C. for 8 hours to give XVII (250 g). Product XVII comprises the acidic organic compounds free acid form 204 of the preferred embodiment shown in FIG. 2.

Composition of XVII

| | |
|---|---|
| 18-Hydroxyoctadec-9-enoic acid | 11.4% |
| 18-Hydroxyl-9,10-epoxyoctadecanoic acid | 43.8% |
| Threo-9,10,18-trihydroxyoctadecanoic acid | 12.1% |
| 22-Hydroxydocosanoic acid | 11.84% |
| Betulinic acid | 12.78% |
| Other ω-hydroxy fatty acids | 8.14% |

Example 4

One-Pot Depolymerization (KOH) and Extraction Technology

Preparation of Crude Neutral Organic Compounds Extract

Pressed outer birch bark (1 kg) was added in portions to a solution of KOH (300 g, 5.35 mol) in $H_2O$ (60 ml) and EtOH (2.0 L) at 70° C. The reaction mixture was refluxed with good stirring for 1 hr. Xylenes (6 L) was then added to the reaction mixture. A solution of EtOH and $H_2O$ in xylenes (3.6 L) was distilled from the reaction mixture. Distillation was continued until temperature of vapors reached 133° C. An additional amount of $H_2O$ (15 ml) was distilled from the reaction mixture using a Dean-Stark receiver. The reaction mixture was filtered at 100° C. The solid residue was added to xylenes (3 L) and refluxed for 1 hr. Water (15 ml) was distilled from the reaction mixture using a Dean-Stark receiver and the reaction mixture filtered at 100° C. Washing of solid residue with xylenes (3 L) was repeated. The combined xylenes extracts was evaporated and dried in vacuum at 80° C. to give XVIII (217 g). The crude neutral organic compounds extract XVIII comprises the neutral organic compounds dissolved in xylenes of the concentrated extract 176 of the preferred embodiment shown in FIG. 2.

Composition of XVIII: Lupeol 7.65%; Betulin 86.0%; Others 6.35%.

Preparation of Betulin 97%+

Pressed outer birch bark (1 kg) was added in portions to a solution of KOH (300 g, 5.35 mol) in $H_2O$ (60 ml) and EtOH (2.0 L) at 70° C. The reaction mixture was refluxed with good stirring for 1 hr. Xylenes (6 L) was then added to the reaction mixture. A solution of EtOH and $H_2O$ in xylenes (3.6 L) was distilled from the reaction mixture. Distillation was continued until temperature of vapors reached 133° C. An additional amount of $H_2O$ (15 ml) was distilled from the reaction mixture using a Dean-Stark receiver. The reaction mixture was filtered at 80° C. The solid residue was added to xylenes (3 L) and refluxed for 1 hr. Water (15 ml) was distilled from the reaction mixture using a Dean-Stark receiver and the reaction mixture was filtered at 80° C. Washing of the solid residue with xylenes (3 L) was repeated. The combined xylenes extracts was heated and a portion of the xylenes (6 L) was evaporated. Betulin was allowed to crystallize from the xylenes solution at room temperature overnight. The xylenes solution was filtered and the solid residue was dried in vacuum at 80° C. to give XIX (180 g, 18%). The product XIX comprises the betulin 190 of the preferred embodiment shown in FIG. 2.

Composition of XIX: Lupeol 1%; Betulin 97%; Others 2%.

Preparation of Lupeol Fraction

Pressed outer birch bark (1 kg) was added in portions to a solution of KOH (300 g, 5.35 mol) in $H_2O$ (60 ml) and EtOH (2.0 L) at 70° C. The reaction mixture was refluxed with good stirring for 1 hr. Xylenes (6 L) was then added to the reaction mixture. A solution of EtOH and $H_2O$ in xylenes (3.6 L) was distilled from the reaction mixture. Distillation was continued until temperature of vapors reached 133° C. An additional amount of $H_2O$ (15 ml) was distilled from the reaction mixture using a Dean-Stark receiver. The reaction mixture was filtrated at 80° C. The solid residue was added to xylenes (3 L) and refluxed for 1 hr. Water (15 ml) was distilled from the reaction mixture using a Dean-Stark receiver and the reaction mixture was filtered at 80° C. Washing of the solid residue with xylenes (3 L) was repeated. The combined xylenes extracts was heated and a portion of the xylenes (6 L) was evaporated. Betulin was allowed to crystallize from the xylenes solution at room temperature overnight. The xylenes solution and mother liquor was evaporated to a volume of about 150 ml, and additional betulin was allowed to crystallize from the mother liquor at room temperature. After filtration, the solid residue was dried under vacuum at 80° C. to give betulin (12.4 g, 1.2%, purity is 80%). The mother liquor was evaporated and dried under vacuum at 80° C. to give XX (24.5 g, 2%). Product XX comprises lupeol 200 of the preferred embodiment shown in FIG. 2.

Composition of XX: Lupeol 52.9%; Betulin 1.9%; Others 45.2%.

Preparation of Suberinic and Betulinic Acids Potassium Salts

Pressed outer birch bark (1 kg) was added in portions to a solution of KOH (300 g, 5.35 mol) in $H_2O$ (60 ml) and EtOH (2.0 L) at 70° C. The reaction mixture was refluxed with good stirring for 1 hr. Xylenes (6 L) was then added to the reaction mixture. A solution of EtOH and $H_2O$ in xylenes (3.6 L) was distilled from the reaction mixture. Distillation was continued until temperature of vapors reached 133° C. An additional amount of $H_2O$ (15 ml) was distilled from the reaction mixture using a Dean-Stark receiver. The reaction mixture was filtered at 80° C. The solid residue was added to xylenes (3 L) and refluxed for 1 hr. Water (15 ml) was distilled from the reaction mixture using a Dean-Stark receiver and the reaction mixture was filtered at 80° C. Washing of the solid residue with xylenes (3 L) was repeated. The solid residue after extraction with xylenes was added to ethanol (8 liters) and refluxed for 1 hr. The reaction mixture was filtered at 70° C. and the solid residue was refluxed for 1 hr in ethanol (4 L). The reaction mixture was filtrated at 70° C. The solid residue was added to ethanol (4 L), refluxed for 1 hr and then filtered at 70° C. The combined ethanol solutions were evaporated and the residue dried under vacuum at 80° C. to give XXI (433 g). Product XXI comprises the acidic organic compounds salt form 174 of the preferred embodiment shown in FIG. 2.

Composition of XXI

| | |
|---|---|
| 18-Hydroxyoctadec-9-enoic acid, potassium salt | 10.5% |
| 18-hydroxy-9,10-epoxyoctadecanoic acid, potassium salt | 40% |
| Threo-9,10,18-trihydroxyoctadecanoic acid, potassium salt | 10% |
| 22-Hydroxydocosanoic acid, potassium salt | 12% |
| Betulinic acid, potassium salt | 8% |
| Other hydroxy fatty acids, potassium salts | 17% |

Preparation of Suberinic and Betulinic Free Acids

Pressed outer birch bark (1 kg) was added in portions to a solution of KOH (300 g, 5.35 mol) in $H_2O$ (60 ml) and EtOH (2.0 L) at 70° C. The reaction mixture was refluxed with good stirring for 1 hr. Xylenes (6 L) was then added to the reaction mixture. A solution of EtOH and $H_2O$ in xylenes (3.6 L) was distilled from the reaction mixture. Distillation was continued until temperature of vapors reached 133° C. An additional amount of $H_2O$ (15 ml) was distilled from the reaction mixture using a Dean-Stark receiver. The reaction mixture was filtered at 80° C. The solid residue was added to xylenes (3 L) and refluxed for 1 hr. Water (15 ml) was distilled from the reaction mixture using a Dean-Stark receiver and the reaction mixture was filtered at 80° C. Washing of the solid residue with xylenes (3 L) was repeated. The solid residue after extraction with xylenes was added to ethanol (8 L) and refluxed for 1 hr. The mixture was filtered at 70° C. and the extraction with EtOH was repeated twice using 4 L of EtOH. After filtration at 70° C., the combined ethanol solutions were evaporated and the residue cidified with a 2% solution of HCl in water (2.5 L). The precipitate was separated by filtration, washed twice with water (1 L), and dried at 40-45° C. under vacuum (200 mm Hg) for 8 hours giving XXII (341 g)

Composition of XXII

| | |
|---|---|
| 18-Hydroxyoctadec-9-enoic acid | 10.14% |
| 18-Hydroxy-9,10-epoxyoctadecanoic acid | 40.8% |
| Threo-9,10,18-trihydroxyoctadecanoic acid | 10.1% |
| 22-Hydroxydocosanoic acid | 12.6% |
| Betulinic acid | 7.98% |
| Other ω-hydroxy fatty acids | 18.38% |

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A process for extracting a neutral organic compound from birch bark, comprising:
   physically processing birch bark comprising one or more of pelletizing the bark, baling the bark, pucking the bark, or compressing the bark to a more dense form than prior to the processing;
   contacting the bark with a mixture of an alkaline aqueous solution and a water-soluble organic solvent, wherein the step of contacting comprises heating the bark in the mixture and optionally comprises soaking the bark in the mixture;
   separating undissolved bark portions, optionally by filtering, and optionally further comprising a step of washing of the undissolved portions of the bark with the water-soluble organic solvent;
   removing substantially all of the water-soluble organic solvent;
   adding a water-insoluble solvent, wherein the water-insoluble solvent comprises hexane, heptane, octane, nonane, toluene, xylenes, benzene, or a combination thereof;
   removing water to obtain a dried water-insoluble solvent extract;
   separating insoluble material, and optionally, in the same step separating of undissolved bark portions, wherein the separating is optionally carried out by filtering;
   removing a major portion of the water-insoluble solvent to yield a concentrated extract; and
   recovering the neutral organic compound from the concentrated extract.

2. The process of claim 1 wherein the step of removing substantially all of the water-soluble organic solvent to yield a solid residue is carried out prior to the step of adding a water-insoluble solvent.

3. The process of claim 1 wherein the step of removing substantially all of the water-soluble organic solvent to yield an extract suspension is carried out after the step of adding a water-insoluble solvent.

4. The process of claim 1 wherein the step of recovering the neutral organic compound comprises a step of crystallizing the neutral organic compound, by refrigerating the concentrated extract that comprises the neutral organic compound, and optionally wherein the recovering comprises filtration.

5. The process of claim 4 wherein the step of filtration further provides a filtrate, the filtrate comprising a second neutral organic compound, which is lupeol.

6. The process of claim 1 wherein the water-soluble organic solvent comprises methanol, ethanol, isopropanol, n-propanol, n-butanol, isobutanol, sec-butanol, or tert-butanol.

7. The process of claim 1 wherein the alkaline aqueous solution comprises a water solution of a metal hydroxide salt, wherein the metal is lithium, sodium, potassium, magnesium, calcium, barium, or a combination thereof.

8. The process of claim 1 wherein the ratio of the alkaline aqueous solution to the water-soluble organic solvent is less than about 1:10 by volume, and wherein the alkaline aqueous solution comprises a water solution with a concentration of the hydroxide salt of greater than about 30% by weight.

9. The process of claim 1 wherein the step of contacting comprises heating the bark in the mixture to a boiling point of the mixture.

10. The process of claim 1 wherein the step of removing substantially all of the water-soluble organic solvent comprises a step of distilling the water-soluble organic solvent.

11. The process of claim 1 wherein the water-insoluble solvent forms an azeotrope with water in the removing water step.

12. The process of claim 1 wherein the water-insoluble solvent possesses a boiling point at atmospheric pressure of greater than about 100° C.

13. The process of claim 1 wherein the neutral organic compound comprises betulin, lupeol, or both.

* * * * *